US012560866B2

(12) United States Patent
Nemoto et al.

(10) Patent No.: US 12,560,866 B2
(45) Date of Patent: Feb. 24, 2026

(54) RADIATION-SENSITIVE RESIN COMPOSITION, METHOD OF FORMING RESIST PATTERN, POLYMER, AND COMPOUND

(71) Applicant: JSR CORPORATION, Tokyo (JP)

(72) Inventors: Ryuichi Nemoto, Tokyo (JP); Ryotaro Tanaka, Tokyo (JP); Taiichi Furukawa, Tokyo (JP); Katsuaki Nishikori, Tokyo (JP); Hiromitsu Nakashima, Tokyo (JP)

(73) Assignee: JSR CORPORATION, Tokyo (JP)

( * ) Notice: Subject to any disclaimer, the term of this patent is extended or adjusted under 35 U.S.C. 154(b) by 935 days.

(21) Appl. No.: 17/829,531

(22) Filed: Jun. 1, 2022

(65) Prior Publication Data

US 2022/0299873 A1 Sep. 22, 2022

Related U.S. Application Data

(63) Continuation of application No. PCT/JP2020/043493, filed on Nov. 20, 2020.

(30) Foreign Application Priority Data

Dec. 4, 2019 (JP) ................................ 2019-219974

(51) Int. Cl.

| | |
|---|---|
| ***G03F 7/039*** | (2006.01) |
| ***C07C 69/734*** | (2006.01) |
| ***C07C 69/736*** | (2006.01) |
| ***C07C 69/96*** | (2006.01) |
| ***C07D 307/00*** | (2006.01) |
| ***C08F 212/14*** | (2006.01) |
| ***C08F 220/10*** | (2006.01) |
| ***C08F 220/28*** | (2006.01) |
| ***C08F 220/30*** | (2006.01) |
| ***C08F 220/36*** | (2006.01) |
| ***C08F 220/38*** | (2006.01) |
| ***G03F 7/038*** | (2006.01) |

(52) U.S. Cl.

CPC ............ *G03F 7/039* (2013.01); *C07C 69/734* (2013.01); *C07C 69/736* (2013.01); *C07C 69/96* (2013.01); *C07D 307/00* (2013.01); *C08F 212/22* (2020.02); *C08F 220/282* (2020.02); *C08F 220/283* (2020.02); *C08F 220/303* (2020.02); *C08F 220/365* (2020.02); *C08F 220/382* (2020.02); *G03F 7/038* (2013.01); *C07C 2601/08* (2017.05); *C07C 2601/14* (2017.05); *C07C 2603/74* (2017.05)

(58) Field of Classification Search

CPC ...... G03F 7/039; G03F 7/038; C08F 220/283; C08F 220/303; C08F 220/282; C08F 220/382; C08F 220/365; C08F 212/22; C07C 69/734; C07C 69/736; C07C 69/96; C07C 2601/08; C07C 2601/14; C07C 2603/74; C07D 307/00

USPC .......................................................... 430/544

See application file for complete search history.

(56) References Cited

U.S. PATENT DOCUMENTS

2012/0016095 A1* 1/2012 Saito ....................... C07C 67/31 526/309

FOREIGN PATENT DOCUMENTS

| | | | | | |
|---|---|---|---|---|---|
| JP | S59-93448 | A | | 5/1984 | |
| JP | H06-12452 | B2 | | 2/1994 | |
| JP | 2004035865 | A | * | 2/2004 | |
| JP | 2009014815 | A | | 1/2009 | |
| JP | 2013200560 | A | | 10/2013 | |
| JP | 2014040585 | A | * | 3/2014 | |
| JP | 2018013744 | A | | 1/2018 | |
| JP | 2018028574 | A | | 2/2018 | |
| WO | WO-2021111912 | A1 | * | 6/2021 | ........... C07D 333/78 |

OTHER PUBLICATIONS

Office Action issued Oct. 4, 2024 in Korean Patent Application No. 10-2022-7015233 (with English translation), 7 pages.

International Search Report issued Jan. 26, 2021 in PCT/JP2020/043493 (with English translation), 7 pages.

(Continued)

*Primary Examiner* — Mark F. Huff
*Assistant Examiner* — Christine Curiac
(74) *Attorney, Agent, or Firm* — Element IP, PLC

(57) ABSTRACT

A radiation-sensitive resin composition includes: a first polymer including a structural unit including an acid-labile group; a second polymer including a structural unit represented by formula (1); and a radiation-sensitive acid generator. In the formula (1), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group including a fluorine atom.

(1)

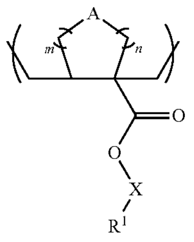

18 Claims, No Drawings

(56) References Cited

OTHER PUBLICATIONS

Written Opinion issued Jan. 26, 2021 in PCT/JP2020/043493 (with English translation), 6 pages.
Office Action and Search Report issued Mar. 25, 2024 in Taiwanese Patent Application No. 109141461 (with English translation), 10 pages.

* cited by examiner

RADIATION-SENSITIVE RESIN COMPOSITION, METHOD OF FORMING RESIST PATTERN, POLYMER, AND COMPOUND

CROSS-REFERENCE TO RELATED APPLICATIONS

The present application is a continuation application of International Application No. PCT/JP2020/043493, filed Nov. 20, 2020, which claims priority to Japanese Patent Application No. 2019-219974, filed Dec. 4, 2019. The contents of these applications are incorporated herein by reference in their entirety.

BACKGROUND OF THE INVENTION

Field of the Invention

The present invention relates to a radiation-sensitive resin composition, a method of forming a resist pattern, a polymer, and a compound.

Description of the Related Art

A radiation-sensitive resin composition for use in microfabrication by lithography generates an acid at a light-exposed region upon an irradiation with a radioactive ray, e.g., an electromagnetic wave such as a far ultraviolet ray such as an ArF excimer laser beam (wavelength of 193 nm), a KrF excimer laser beam (wavelength of 248 nm), etc., an extreme ultraviolet ray (EUV), or a charged particle ray such as an electron beam. A chemical reaction in which the acid serves as a catalyst causes a difference in rates of dissolution in a developer solution between light-exposed regions and light-unexposed regions, whereby a resist pattern is formed on a substrate.

Such a radiation-sensitive resin composition is required not only to have favorable sensitivity to exposure light, but also to have superiority in terms of each of LWR (Line Width Roughness) performance, which indicates line width uniformity, and CDU (Critical Dimension Uniformity) performance, which indicates variance of line widths in greater ranges. To meet such requirements, types, molecular structures, and the like of polymers, acid generating agents, and other components which may be used in radiation-sensitive resin compositions have been investigated (see Japanese Unexamined Patent Publication, Publication Nos. 2009-14815 and 2013-200560).

SUMMARY OF THE INVENTION

According to an aspect of the present invention, a radiation-sensitive resin composition includes: a first polymer including a structural unit including an acid-labile group; a second polymer including a structural unit represented by formula (1); and a radiation-sensitive acid generator.

(1)

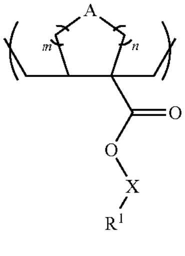

In the formula (1), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group including a fluorine atom.

According to another aspect of the present invention, a method of forming a resist pattern, includes: applying a radiation-sensitive resin composition directly or indirectly on a substrate to form a resist film; exposing the resist film; and developing the resist film exposed. The radiation-sensitive resin composition includes: a first polymer including a structural unit including an acid-labile group; a second polymer including a structural unit represented by formula (1); and a radiation-sensitive acid generator.

(1)

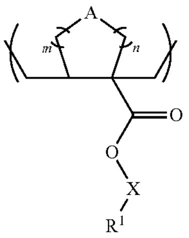

In the formula (1), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group including a fluorine atom.

According to a further aspect of the present invention, a polymer includes a structural unit represented by formula (1).

(1)

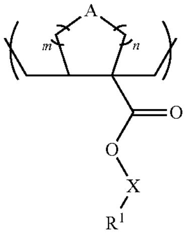

In the formula (1), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group including a fluorine atom.

According to a further aspect of the present invention, a compound is represented by formula (i).

(i)

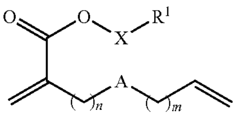

In the formula (i), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group including a fluorine atom.

DESCRIPTION OF THE EMBODIMENTS

As used herein, the words "a" and "an" and the like carry the meaning of "one or more." When an amount, concentration, or other value or parameter is given as a range, and/or its description includes a list of upper and lower values, this is to be understood as specifically disclosing all integers and fractions within the given range, and all ranges formed from any pair of any upper and lower values, regardless of whether subranges are separately disclosed. Where a range of numerical values is recited herein, unless otherwise stated, the range is intended to include the endpoints thereof, as well as all integers and fractions within the range. As an example, a stated range of 1-10 fully describes and includes the independent subrange 3.4-7.2 as does the following list of values: 1, 4, 6, 10.

Under current circumstances in which miniaturization of resist patterns has proceeded to a level in which line widths are 40 nm or less, in addition to the aforementioned types of performance, radiation-sensitive resin compositions are required to enable forming a resist pattern having superior water repellency and few defects.

One embodiment of the invention is a radiation-sensitive resin composition containing: a first polymer (hereinafter, may be also referred to as "(A) polymer" or "polymer (A)") having a structural unit (hereinafter, may be also referred to as "structural unit (I)") including an acid labile group; and a second polymer (hereinafter, may be also referred to as "(E) polymer" or "polymer (E)") having a second structural unit (hereinafter, may be also referred to as "structural unit (T)") represented by the following formula (1); and a radiation-sensitive acid generator (hereinafter, may be also referred to as "(B) acid generator" or "acid generator (B)").

(1)

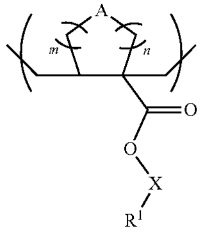

In the above formula (1), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group having a fluorine atom.

According to an other embodiment of the invention, a method of forming a resist pattern includes: applying a radiation-sensitive resin composition directly or indirectly on a substrate; exposing a resist film formed by the applying; and developing the resist film exposed, wherein the radiation-sensitive resin composition contains: the polymer (A), the polymer (E), and the acid generator (B).

Still another embodiment of the invention is the polymer (E) having the structural unit (T).

Yet another embodiment of the invention is a compound (hereinafter, may be also referred to as "compound (F)") represented by the following formula (i).

(i)

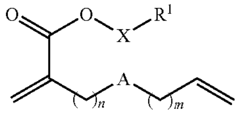

In the above formula (i), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group having a fluorine atom.

The radiation-sensitive resin composition, the method of forming a resist pattern, the polymer, and the compound of the embodiments of the present invention enable formation of a resist pattern with favorable sensitivity to exposure light, and having superior water repellency and a property of enabling formation of a resist pattern having few defects (hereinafter, may be also referred to as "defect-inhibiting property"). Thus, these can be suitably used in manufacturing of a semiconductor device and the like, in which further progress of miniaturization is expected in the future. Hereinafter, the embodiments of the present invention will be described in detail.

Radiation-Sensitive Resin Composition

The radiation-sensitive resin composition of one embodiment of the present invention contains the polymer (A), the polymer (E), and the acid generator (B). The radiation-sensitive resin composition may contain, as favorable components, an acid diffusion controller (C) and a solvent (D), and may contain, within a range not leading to impairment of the effects of the present invention, other optional component(s).

Due to containing the polymer (A), the polymer (E), and the acid generator (B), the radiation-sensitive resin composition has favorable sensitivity to exposure light, and enables formation of a resist pattern having superior water repellency and few defects. Although not necessarily clarified and without wishing to be bound by any theory, the reason for achieving the aforementioned effects by the radiation-sensitive resin composition due to involving such a constitution may be presumed, for example, as in the following. It is considered that owing to the structural unit (T) in the polymer (E) contained in the radiation-sensitive resin composition, the sensitivity improves, and in addition, a highly water repellent property and the defect-inhibiting property can be exhibited. Hereinafter, each component of the radiation-sensitive resin composition will be described.

(A) Polymer

The polymer (A) is a polymer having the structural unit (I). In addition to the structural unit (I), the polymer (A) may have, as preferable optional components: a structural unit (hereinafter, may be also referred to as "structural unit (II)") including a lactone structure, a cyclic carbonate structure, a sultone structure, or a combination thereof; a structural unit (hereinafter, may be also referred to as "structural unit (III)") including an alcoholic hydroxyl group; a structural unit (hereinafter, may be also referred to as "structural unit (IV)") including a phenolic hydroxyl group; and/or the like. The polymer (A) may have other structural unit(s) aside from the structural units (I) to (IV). The polymer (A) may have one, or two or more types of each structural unit. Each structural unit will be described below.

Structural Unit (I)

The structural unit (I) is a structural unit including an acid-labile group. The "acid-labile group" as referred to herein means a group that substitutes for a hydrogen atom of a carboxy group or a phenolic hydroxyl group, and is dissociable by an action of an acid. When the polymer (A) has the acid-labile group in the structural unit (I), the acid-labile group is dissociated in light-exposed regions by an action of an acid generated in the exposing, and a difference in solubility in a developer solution emerges between the light-exposed regions and the light-unexposed regions, thereby enabling forming the resist pattern.

The structural unit (I) is exemplified by structural units (hereinafter, may be also referred to as "structural units (I-1A), (I-1B), (I-2A), and (I-2B)") represented by the following formulae (2-1A), (2-1B), (2-2A), and (2-2B), and the like. It is to be noted that in the structural units (I-1A) to (I-2B), $-CR^XR^YR^Z$ or $-CR^UR^V(OR^W)$ bonding to an oxy-oxygen atom derived from the carboxy group or the phenolic hydroxyl group corresponds to the acid-labile group.

(2-1A)

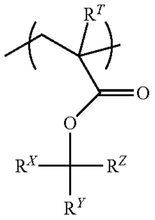

(2-1B)

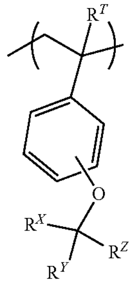

(2-2A)

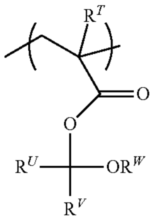

(2-2B)

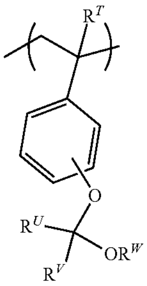

In the above formulae (2-1A) and (2-1B), $R^T$ represents a hydrogen atom, a fluorine atom, a methyl group, or a trifluoromethyl group; $R^X$ represents a monovalent hydrocarbon group having 1 to 20 carbon atoms; and $R^Y$ and $R^Z$ each independently represent a monovalent hydrocarbon group having 1 to 20 carbon atoms, or $R^Y$ and $R^Z$ taken together represent an alicyclic structure having 3 to 20 ring atoms, together with the carbon atom to which $R^Y$ and $R^Z$ bond.

In the above formulae (2-2A) and (2-2B), $R^T$ represents a hydrogen atom, a fluorine atom, a methyl group, or a trifluoromethyl group; $R^U$ represents a hydrogen atom or a monovalent hydrocarbon group having 1 to 20 carbon atoms; and $R^V$ and $R^W$ each independently represent a monovalent hydrocarbon group having 1 to 20 carbon atoms, or $R^V$ and $R^W$ taken together represent an aliphatic heterocyclic structure having 4 to 20 ring atoms, together with the carbon atom to which $R^U$ bonds and the oxygen atom adjacent to this carbon atom.

The monovalent hydrocarbon group having 1 to 20 carbon atoms which may be represented by $R^X$, $R^Y$, $R^Z$, $R^U$, $R^V$, or $R^W$ may be exemplified by a monovalent chain hydrocarbon group having 1 to 20 carbon atoms, a monovalent alicyclic hydrocarbon group having 3 to 20 carbon atoms, a monovalent aromatic hydrocarbon group having 6 to 20 carbon atoms, and the like. It is to be noted that the "alicyclic hydrocarbon group" as referred to herein is not necessarily constituted with only an alicyclic structure, and a chain structure may be contained in a part thereof. Furthermore, the "aromatic hydrocarbon group" as referred to herein is not necessarily constituted with only an aromatic ring structure, and may contain a chain structure and/or an alicyclic structure in a part thereof.

Examples of the monovalent chain hydrocarbon group having 1 to 20 carbon atoms include: alkyl groups such as a methyl group, an ethyl group, an n-propyl group, and an i-propyl group; alkenyl groups such as an ethenyl group and a propenyl group; alkynyl groups such as an ethynyl group and a propynyl group; and the like. Examples of the monovalent alicyclic hydrocarbon group having 3 to 20 carbon atoms include: alicyclic saturated hydrocarbon groups such as a cyclopropyl group, a cyclobutyl group, cyclopentyl group, a cyclohexyl group, a norbornyl group, and an adamantyl group; alicyclic unsaturated hydrocarbon groups such as a cyclopropenyl group, a cyclobutenyl group, cyclopentenyl group, a cyclohexenyl group, and a norbornenyl group; and the like. Examples of the monovalent aromatic hydrocarbon group having 6 to 20 carbon atoms include: aryl groups such as a phenyl group, a tolyl group, a xylyl group, a naphthyl group, and an anthryl group; aralkyl groups such as a benzyl group, a phenethyl group, a naphthylmethyl group, and an anthrylmethyl group; and the like.

Examples of the alicyclic structure having 3 to 20 ring atoms which may be represented by $R^Y$ and $R^Z$ taken together, together with the carbon atom to which $R^Y$ and $R^Z$ bond include: saturated alicyclic structures such as a cyclopropane structure, a cyclobutane structure, a cyclopentane structure, a cyclohexane structure, a norbornane structure, and an adamantane structure; unsaturated alicyclic structures such as a cyclopropene structure, a cyclobutene structure, a cyclopentene structure, a cyclohexene structure, and a norbornene structure; heterocyclic structures such as a cyclic ether structure, a lactone structure, a cyclic carbonate structure, and a sultone structure; and the like.

Examples of the aliphatic heterocyclic structure having 4 to 20 ring atoms which may be represented by $R^V$ and $R^W$ taken together, together with the carbon atom to which $R^U$ bonds and the oxygen atom adjacent to this carbon atom include: oxacycloalkane structures such as an oxacyclobutane structure, an oxacyclopentane structure, and an oxacyclohexane structure; oxacycloalkene structures such as an oxacyclobutene structure, an oxacyclopentene structure, and an oxacyclohexene structure; lactone structures; and the like.

In light of copolymerizability of a monomer that gives the structural unit (I), $R^T$ represents preferably a hydrogen atom or a methyl group. $R^X$ represents preferably a hydrogen atom, an alkyl group, or an aryl group. $R^Y$ and $R^Z$ represent preferably an alkyl group or the alicyclic saturated hydrocarbon group. The structural unit (I) is preferably the structural unit (I-1A).

Examples of the structural unit (I) include structural units derived from, as monomers, compounds represented by the formulae (m-1) to (m-4) and (m-20) disclosed in EXAMPLES, described later, and the like. In addition, examples of the structural unit (I) include, of structural units exemplified as the structural unit (I) in Japanese Unexamined Patent Application, Publication No. 2018-013744, structural units corresponding to the above formulae (2-1A), (2-1B), (2-2A), and (2-2B), and the like.

The lower limit of a proportion of the structural unit (I) with respect to total structural units constituting the polymer (A) is preferably 5 mol %, more preferably 10 mol %, still more preferably 20 mol %, and particularly preferably 30 mol %. The upper limit of the proportion is preferably 80 mol %, more preferably 70 mol %, and still more preferably 60 mol %. This proportion is particularly preferred in a case in which the exposure light is an ArF excimer laser beam. In a case in which the exposure light is EUV, the lower limit of the proportion with respect to total structural units is preferably 10 mol %, and more preferably 20 mol %. The upper limit of the proportion is preferably 70 mol %, and more preferably 60 mol %. When the proportion of the structural unit (I) falls within the above ranges, the sensitivity of the radiation-sensitive resin composition to exposure light can be further improved, and moreover, the highly water repellent property and the defect-inhibiting property can be further improved.

Structural Unit (II)

The structural unit (II) is a structural unit other than the structural unit (I), and includes a lactone structure, a cyclic carbonate structure, a sultone structure, or a combination thereof. When the polymer (A) has the structural unit (II), the solubility of the polymer (A) in a developer solution becomes easier to adjust in a more appropriate manner, and as a result, the sensitivity of the radiation-sensitive resin composition to exposure light can be further improved, and the highly water repellent property and the defect-inhibiting property can be further improved.

Examples of the structural unit (II) include structural units derived from, as monomers, compounds represented by the formulae (m-5) to (m-11) and (m-13) disclosed in EXAMPLES, described later, and the like. In addition, examples of the structural unit (II) include structural units exemplified as the structural unit (III) in Japanese Unexamined Patent Application, Publication No. 2018-013744, and the like.

The lower limit of a proportion of the structural unit (II) with respect to total structural units in the polymer (A) is preferably 5 mol %, more preferably 10 mol %, still more preferably 20 mol %, and particularly preferably 30 mol %. The upper limit of the proportion is preferably 80 mol %, and more preferably 70 mol %. When the proportion of the structural unit (II) falls within the above range, the solubility of the polymer (A) in a developer solution becomes easier to adjust in a still more appropriate manner, and as a result, the highly water repellent property and the defect-inhibiting property can be still further improved.

Structural Unit (III)

The structural unit (III) is a structural unit other than the structural unit (I) and the structural unit (II), and includes an alcoholic hydroxyl group. When the polymer (A) has the structural unit (III), the solubility of the polymer (A) in a developer solution becomes easier to adjust in a more appropriate manner, and as a result, the highly water repellent property and the defect-inhibiting property of the radiation-sensitive resin composition can be further improved.

Examples of the structural unit (III) include structural units derived from, as monomers, compounds represented by the formulae (m-12) and (m-14) disclosed in EXAMPLES, described later, and the like. In addition, examples of the structural unit (III) include structural units exemplified as the structural unit (IV) in Japanese Unexamined Patent Application, Publication No. 2018-028574, and the like.

The lower limit of a proportion of the structural unit (III) with respect to total structural units constituting the polymer (A) is preferably 5 mol %, and more preferably 10 mol %. The upper limit of the proportion is preferably 40 mol %, and more preferably 30 mol %. This proportion is particularly preferred in a case in which the exposure light is an ArF excimer laser beam. In a case in which the exposure light is EUV, the lower limit of the proportion with respect to total structural units is preferably 5 mol %, more preferably 10 mol %, and still more preferably 20 mol %. The upper limit of the proportion is preferably 60 mol %, more preferably 50 mol %, and still more preferably 40 mol %. When the proportion of the structural unit (III) falls within the above ranges, the solubility of the polymer (A) in a developer solution becomes easier to adjust in an even more appropriate manner, and as a result, the highly water repellent property and the defect-inhibiting property of the radiation-sensitive resin composition can be still further improved.

Structural Unit (IV)

The structural unit (IV) is a structural unit other than the structural unit (I), the structural unit (II), and the structural unit (III), and includes a phenolic hydroxyl group. The "phenolic hydroxyl group" as referred to herein is not limited to a hydroxy group directly bonding to a benzene ring, and means any hydroxy group directly bonding to an aromatic ring. In the case of using an ArF excimer laser beam, a KrF excimer laser beam, EUV, an electron beam, or the like as the radioactive ray, the sensitivity to exposure light can be further improved due to the polymer (A) having the structural unit (IV), and as a result, the LWR performance and the CDU performance of the radiation-sensitive resin composition can be further improved. Examples of the structural unit (IV) include structural units represented by the following formula (P), and the like.

(P)

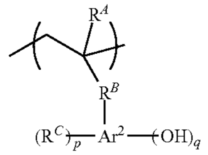

In the above formula (P), $R^A$ represents a hydrogen atom, a fluorine atom, a methyl group, or a trifluoromethyl group; $R^B$ represents a single bond, —O—, —COO—, or —CONH—; $Ar^2$ represents a group obtained by removing (p+q+1) hydrogen atoms on an aromatic ring from an arene having 6 to 20 ring atoms; p is an integer of 0 to 10, wherein in a case in which p is 1, $R^C$ represents a halogen atom or a monovalent organic group having 1 to 20 carbon atoms, in a case in which p is no less than 2, a plurality of $R^C$ s are identical or different from each other and each $R^C$ represents a halogen atom or a monovalent organic group having 1 to 20 carbon atoms, or no less than two of the plurality of $R^C$s taken together represent a ring structure having 4 to 20 ring atoms together with the carbon chain to which the no less than two $R^C$s bond; and q is an integer of 1 to 11, wherein a sum of p and q is no greater than 11.

In light of copolymerizability of a monomer that gives the structural unit (IV), $R^A$ represents preferably a hydrogen atom or a methyl group, and more preferably a hydrogen atom. $R^B$ represents preferably a single bond or —COO—, and more preferably a single bond. Examples of the arene having 6 to 20 ring atoms which gives $Ar^2$ include benzene, naphthalene, anthracene, phenanthrene, tetracene, pyrene, and the like. Of these, benzene or naphthalene is preferred, and benzene is further preferred.

The monovalent organic group having 1 to 20 carbon atoms which may be represented by $R^C$ is exemplified by: a monovalent hydrocarbon group having 1 to 20 carbon atoms; a group which includes a divalent heteroatom-containing group between two adjacent carbon atoms or at the end of the atomic bonding side of the hydrocarbon group; a group obtained by substituting with a monovalent heteroatom-containing group, a part or all of hydrogen atoms included in the hydrocarbon group or the divalent heteroatom-containing group; and the like. $R^C$ represents preferably a hydrocarbon group, and more preferably an alkyl group. Examples of the ring structure having 4 to 20 ring atoms which may be represented by the no less than 2 of the plurality of $R^C$s taken together, together with the carbon chain to which the no less than two $R^C$s bond include an alicyclic structure such as a cyclohexane structure, and the like. p is preferably 0 to 2, more preferably 0 or 1, and more preferably 0. q is preferably 1 to 3, and more preferably 1 or 2.

Examples of the structural unit (IV) include structural units derived from, as monomers, compounds represented by the formulae (m-15) and (m-16) disclosed in EXAMPLES, described later, and the like. In addition, examples of the structural unit (IV) include structural units exemplified as the structural unit (II) in Japanese Unexamined Patent Application, Publication No. 2018-013744, and the like.

The lower limit of a proportion of the structural unit (IV) with respect to total structural units constituting the polymer (A) is preferably 5 mol %, more preferably 10 mol %, and particularly preferably 20 mol %. The upper limit of the proportion is preferably 80 mol %, more preferably 70 mol %, and particularly preferably 60 mol %. When the proportion of the structural unit (IV) falls within the above range, the highly water repellent property and the defect-inhibiting property can be further improved.

Other Structural Unit(s)

The other structural unit(s) is/are exemplified by a structural unit including an acid-nonlabile hydrocarbon group, and the like. Examples of the acid-nonlabile hydrocarbon group include a monovalent chain hydrocarbon group and a monovalent alicyclic hydrocarbon group, each of which bonds to the oxy group of —COO—; and the like. In the case in which the polymer (A) has the other structural unit, the upper limit of a proportion of the other structural unit is preferably 30 mol %, and more preferably 20 mol %. The lower limit of the proportion is, for example, 1 mol %.

The lower limit of a polystyrene-equivalent weight average molecular weight (Mw) of the polymer (A) as determined by gel permeation chromatography (GPC) is preferably 2,000, more preferably 3,000, still more preferably 4,000, and particularly preferably 5,000. The upper limit of the Mw is preferably 30,000, more preferably 20,000, still more preferably 15,000, and particularly preferably 10,000. When the Mw of the polymer (A) falls within the above range, coating characteristics of the radiation-sensitive resin composition can be improved, and as a result, the highly water repellent property and the defect-inhibiting property can be further improved.

The upper limit of a ratio (Mw/Mn) of the Mw to a polystyrene-equivalent number average molecular weight (Mn) of the polymer (A) as determined by GPC is preferably 3.00, more preferably 2.50, still more preferably 2.00, and particularly preferably 1.85. The lower limit of the ratio is typically 1.00, and preferably 1.10.

It is to be noted that the Mw and the Mn of the polymer as referred to herein are values determined using gel permeation chromatography (GPC) under the following conditions.

GPC columns: "G2000 HXL"×2, "G3000 HXL"×1, and "G4000 HXL"×1, available from Tosoh Corporation;
elution solvent: tetrahydrofuran
flow rate: 1.0 mL/min
sample concentration: 1.0% by mass
amount of injected sample: 100 uL
column temperature: 40° C.
detector: differential refractometer
standard substance: mono-dispersed polystyrene The lower limit of a proportion of the polymer (A) with respect to total components other than the solvent (D) in the radiation-sensitive resin composition is preferably 50% by mass, more preferably 70% by mass, and still more preferably 80% by mass. Either one, or two or more types of the polymer (A) can be used.

Method of Synthesizing Polymer (A)

The polymer (A) can be synthesized by, for example, polymerizing a monomer that gives each structural unit according to a well-known procedure.

(E) Polymer

The polymer (E) is a polymer which has the structural unit (T). The polymer (E) is a polymer having a total proportion by mass of fluorine atoms being greater than that of the polymer (A). A polymer having higher hydrophobicity than that of a polymer acting as a base polymer tends to be localized in the surface layer of a resist film; thus, since the polymer (E) has the total proportion by mass of fluorine atoms being greater than that of the polymer (A), the polymer (E) tends to be localized in the surface layer of the resist film due to the characteristics that result from the hydrophobicity. In addition, due to the characteristics that result from the hydrophobicity, a receding contact angle of a liquid immersion medium on the resist film becomes higher. Thus, due to containing the polymer (E), the radiation-sensitive resin composition is suitable for a liquid immersion lithography process, and in addition, forming a resist pattern having superior water repellency and inhibited occurrence of defects is enabled.

The lower limit of the proportion of fluorine atoms in the polymer (E) is preferably 1% by mass, more preferably 2% by mass, and still more preferably 3% by mass. The upper limit of the proportion is preferably 60% by mass, more preferably 50% by mass, and still more preferably 40% by mass. When the total proportion by mass of fluorine atoms falls within the above range, localization of the polymer (E)

in the resist film can be more appropriately adjusted. It is to be noted that the total proportion by mass of fluorine atoms in the polymer may be calculated based on the structure of the polymer determined by $^{13}$C-NMR spectroscopy.

In addition to the structural unit (T), the polymer (E) preferably has the structural unit (I), the structural unit (II), the structural unit (III), and/or the structural unit (IV), each described above, and may have the other structural unit(s) aside from the structural units (I) to (IV). For example, the polymer (E) preferably has a structural unit (hereinafter, may be also referred to as "structural unit (F)") which has a fluorine atom, and is a structural unit other than the structural unit (T). The polymer (E) may have one, or two or more types of each structural unit. Each structural unit will be described below.

Structural Unit (T)

The structural unit (T) is a structural unit represented by the following formula (1). Due to the polymer (E) having the structural unit (T), formation of a resist pattern is enabled with favorable sensitivity to exposure light, and having superior water repellency and few defects.

(1)

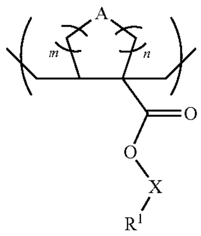

In the above formula (1), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group having a fluorine atom.

A represents preferably an oxygen atom. m is preferably 1, and n is preferably 1 (in other words, the sum of m and n is preferably 2).

X represents preferably a single bond, a substituted or unsubstituted divalent hydrocarbon group having 1 to 20 carbon atoms, a divalent organic group having a lactone structure and having 4 to 20 carbon atoms, —$X^1$—O—, or —$X^2$—NH—, wherein $X^1$ and $X^2$ each independently represent a divalent hydrocarbon group having 1 to 20 carbon atoms.

It is to be noted that in a case in which $R^1$ is defined as (1-2), described below, X represents preferably a single bond, —$X^1$—O—, or —$X^2$—NH—.

Of these, X represents preferably the substituted or unsubstituted divalent hydrocarbon group having 1 to 20 carbon atoms. The divalent hydrocarbon group which may be represented by X is more preferably a chain hydrocarbon group having 1 to 4 carbon atoms, an alicyclic hydrocarbon group having 6 to 10 carbon atoms, or an aromatic hydrocarbon group having 6 to 10 carbon atoms; and particularly preferably a methanediyl group, a cyclohexanediyl group, a norbornanediyl group, an adamantanediyl group, or a benzenediyl group. The divalent hydrocarbon group represented by $X^1$ or $X^2$ is more preferably the chain hydrocarbon group having 1 to 4 carbon atoms.

Examples of the divalent chain hydrocarbon group having 1 to 4 carbon atoms include: alkanediyl groups such as a methanediyl group, an ethanediyl group, an n-propanediyl group, and an i-propanediyl group; alkenediyl groups such as an ethenediyl group and a propenediyl group; alkynediyl groups such as an ethynediyl group and a propynediyl group; and the like. Examples of the divalent alicyclic hydrocarbon group having 6 to 10 carbon atoms include monocyclic cycloalkanediyl groups such as a cyclohexanediyl group; monocyclic cycloalkenediyl groups such as a cyclohexenediyl group; polycyclic cycloalkanediyl groups such as a norbornanediyl group, an adamantanediyl group, and a tricyclodecanediyl group; polycyclic cycloalkenediyl groups such as a norbornenediyl group and a tricyclodecenediyl group; and the like. Examples of the divalent aromatic hydrocarbon group having 6 to 10 carbon atoms include arenediyl groups such as a benzenediyl group, a toluenediyl group, and a naphthenediyl group; arenediylalkanediyl groups such as a benzenediylmethanediyl group; and the like.

The lactone structure which may be contained in X is exemplified by a structure represented by the following formula (X-1) or (X-2), and the like.

(X-1)

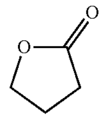

(X-2)

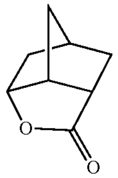

The hydrocarbon group which may be represented by X, $X^1$, or $X^2$ may contain a substituent such as a halogen atom, e.g., a fluorine atom; —COO—$X^3$, wherein $X^3$ represents a monovalent hydrocarbon group having 1 to 20 carbon atoms; or the like. In other words, X, $X^1$, and $X^2$ may each independently represent a divalent hydrocarbon group having 1 to 20 carbon atoms which has been substituted with a substituent such as a halogen atom, —COO—$X^3$, or the like. $X^3$ represents preferably a monovalent chain hydrocarbon group having 1 to 4 carbon atoms.

As $R^1$, a group defined as (1-1) or (1-2) below can be preferably exemplified:

(1-1): a group represented by *—COO—$R^{1a}$, wherein $R^{1a}$ represents a substituted or unsubstituted monovalent fluorinated hydrocarbon group having 1 to 20 carbon atoms, or a monovalent organic group having —O—, —CO—, or —COO— between two carbon atoms in a C—C bond constituting a substituted or unsubstituted monovalent fluorinated hydrocarbon group having 2 to 20 carbon atoms; and * denotes a site of bonding to X in the above formula (1); and (1-2): a substituted or unsubstituted monovalent fluorinated hydrocarbon group having 1 to 20 carbon atoms, or a group having —O—, —CO—, or —COO— between two carbon atoms in a C—C bond constituting a substituted or unsubstituted monovalent fluorinated hydrocarbon group having 2 to 20 carbon atoms, wherein the group defined as (1-2) does not fall under the group defined as (1-1).

$R^{1a}$ in the group defined as (1-1) above represents preferably the substituted or unsubstituted monovalent fluorinated hydrocarbon group having 1 to 20 carbon atoms, —$R^{1b}$—COO—$R^{1c}$, or —$R^{1d}$—O—$R^{1e}$. $R^{1b}$ represents a substituted or unsubstituted divalent hydrocarbon group having 1 to 20 carbon atoms, a substituted or unsubstituted divalent fluorinated hydrocarbon group having 1 to 20 carbon atoms, or a divalent organic group having a lactone structure and having 4 to 20 carbon atoms. $R^{1c}$ represents a substituted or unsubstituted monovalent hydrocarbon group having 1 to 20 carbon atoms or a substituted or unsubstituted monovalent fluorinated hydrocarbon group having 1 to 20 carbon atoms, wherein at least one of $R^{1b}$ and $R^{1c}$ has a fluorine atom. $R^{1d}$ represents a substituted or unsubstituted divalent hydrocarbon group having 1 to 20 carbon atoms, a substituted or unsubstituted divalent fluorinated hydrocarbon group having 1 to 20 carbon atoms, or a divalent organic group having a lactone structure and having 4 to 20 carbon atoms. $R^{1e}$ represents a substituted or unsubstituted monovalent hydrocarbon group having 1 to 20 carbon atoms, a substituted or unsubstituted monovalent fluorinated hydrocarbon group having 1 to 20 carbon atoms, or —$R^{1f}$—O—$R^{1g}$. $R^{1f}$ represents a substituted or unsubstituted divalent hydrocarbon group having 1 to 20 carbon atoms or a substituted or unsubstituted divalent fluorinated hydrocarbon group having 1 to 20 carbon atoms. $R^{1g}$ represents a substituted or unsubstituted monovalent hydrocarbon group having 1 to 20 carbon atoms or a substituted or unsubstituted monovalent fluorinated hydrocarbon group having 1 to 20 carbon atoms, wherein at least one of $R^{1d}$ and $R^{1e}$ has a fluorine atom.

In the case in which $R^{1a}$ represents the substituted or unsubstituted monovalent fluorinated hydrocarbon group having 1 to 20 carbon atoms, the monovalent fluorinated hydrocarbon group may be exemplified by a group obtained by substituting with a fluorine atom, at least one hydrogen atom contained in the monovalent hydrocarbon group having 1 to 20 carbon atoms represented by $R^X$ in the above formula (2-1A), and the like.

In this case, the substituted or unsubstituted monovalent fluorinated hydrocarbon group which may be represented by $R^{1a}$ is preferably a substituted or unsubstituted monovalent chain fluorinated hydrocarbon group having 1 to 6 carbon atoms, a substituted or unsubstituted monovalent alicyclic fluorinated hydrocarbon group having 6 to 10 carbon atoms, or a substituted or unsubstituted monovalent aromatic fluorinated hydrocarbon group having 6 to 10 carbon atoms. The substituent which may be included in $R^{1a}$ is preferably —OH.

In the case in which $R^{1a}$ represents —$R^{1b}$—COO—$R^{1c}$, the divalent hydrocarbon group which may be represented by $R^{1b}$ may be exemplified by groups similar to the divalent hydrocarbon group which may be represented by X, and the like. The divalent fluorinated hydrocarbon group which may be represented by $R^{1b}$ may be exemplified by groups obtained by substituting with a fluorine atom, at least one hydrogen atom contained in groups similar to the divalent hydrocarbon group which may be represented by X, and the like. The lactone structure which may be contained in $R^{1b}$ may be exemplified by structures represented by the above formulae (X-1) and (X-2), and the like. The monovalent fluorinated hydrocarbon group which may be represented by $R^{1c}$ may be exemplified by groups obtained by substituting with a fluorine atom, at least one hydrogen atom contained in the monovalent hydrocarbon group represented by $R^X$ in the above formula (2-1A), and the like.

In this case, $R^{1b}$ represents preferably a substituted or unsubstituted divalent chain hydrocarbon group having 1 to 10 carbon atoms, a substituted or unsubstituted divalent chain fluorinated hydrocarbon group having 1 to 10 carbon atoms, a substituted or unsubstituted divalent alicyclic fluorinated hydrocarbon group having 5 to 10 carbon atoms, or a divalent organic group having a lactone structure and having 6 to 10 carbon atoms. $R^{1c}$ represents preferably a substituted or unsubstituted monovalent chain hydrocarbon group having 1 to 4 carbon atoms, a substituted or unsubstituted monovalent aromatic hydrocarbon group having 6 to 10 carbon atoms, or a substituted or unsubstituted monovalent chain fluorinated hydrocarbon group having 1 to 4 carbon atoms.

Each substituent which may be included in $R^{1b}$ and $R^{1c}$ independently represents preferably —OH, COO—$R^{1b}$, or —O—$R^{1i}$. $R^{1b}$ represents a divalent hydrocarbon group having 1 to 20 carbon atoms. $R^{1i}$ represents a monovalent hydrocarbon group having 1 to 20 carbon atoms. The divalent hydrocarbon group which may be represented by $R^{1g}$ may be exemplified by groups similar to the divalent hydrocarbon group in X, and the like. The monovalent hydrocarbon group represented by $R^{1i}$ may be exemplified by groups similar to the monovalent hydrocarbon group represented by $R^X$ in the above formula (2-1A), and the like. $R^{1b}$ represents preferably a divalent chain hydrocarbon group having 1 to 4 carbon atoms. $R^{1i}$ represents preferably a monovalent chain hydrocarbon group having 1 to 4 carbon atoms.

In the case in which $R^{1a}$ represents —$R^{1d}$—O—$R^{1e}$, the divalent hydrocarbon group which may be represented by $R^{id}$ may be exemplified by groups similar to the divalent hydrocarbon group which may be represented by X, and the like. The divalent fluorinated hydrocarbon group which may be represented by $R^{1d}$ may be exemplified by groups obtained by substituting with a fluorine atom, at least one hydrogen atom contained in groups similar to the divalent hydrocarbon group which may be represented by X, and the like. The lactone structure which may be contained in $R^{1d}$ may be exemplified by the structures represented by the above formulae (X-1) and (X-2), and the like. The monovalent hydrocarbon group which may be represented by $R^{1e}$ may be exemplified by groups similar to the monovalent hydrocarbon group represented by $R^X$ in the above formula (2-1A), and the like. The monovalent fluorinated hydrocarbon group which may be represented by $R^{1e}$ may be exemplified by groups obtained by substituting with a fluorine atom, at least one hydrogen atom contained in the monovalent hydrocarbon group represented by $R^X$ in the above formula (2-1A), and the like. In the case in which $R^{1e}$ represents —$R^{1f}$—O—$R^{1g}$, the divalent hydrocarbon group which may be represented by $R^{1f}$ may be exemplified by groups similar to the divalent hydrocarbon group in X, and the like. The divalent fluorinated hydrocarbon group which may be represented by $R^{1f}$ may be exemplified by groups obtained by substituting with a fluorine atom, at least one hydrogen atom contained in groups similar to the divalent hydrocarbon group which may be represented by X, and the like. The monovalent hydrocarbon group which may be represented by $R^{1g}$ may be exemplified by groups similar to the monovalent hydrocarbon group represented by $R^X$ in the above formula (2-1A), and the like. The monovalent fluorinated hydrocarbon group which may be represented by $R^{1g}$ may be exemplified by groups obtained by substituting with a fluorine atom, at least one hydrogen atom contained in the monovalent hydrocarbon group represented by $R^X$ in the above formula (2-1A), and the like.

In this case, $R^{id}$ represents preferably a substituted or unsubstituted divalent chain fluorinated hydrocarbon group having 1 to 4 carbon atoms. In the case in which $R^{1e}$ represents the substituted or unsubstituted monovalent hydrocarbon group having 1 to 20 carbon atoms, the monovalent hydrocarbon group represented by $R^{1e}$ is preferably a monovalent chain hydrocarbon group having 1 to 4 carbon atoms. In the case in which $R^{1e}$ represents —$R^{1f}$—O—$R^{1g}$, the divalent hydrocarbon group which may be represented by $R^{1f}$ is preferably a divalent chain hydrocarbon group having 1 to 4 carbon atoms, and the monovalent hydrocarbon group which may be represented by $R^{1g}$ is preferably a monovalent chain hydrocarbon group having 1 to 4 carbon atoms. Each substituent which may be included in $R^{1d}$, $R^{1e}$, $R^{1f}$, and $R^{1g}$ is preferably independently —OH.

The group defined as (1-2) is preferably the substituted or unsubstituted monovalent fluorinated hydrocarbon group having 1 to 20 carbon atoms,*—CO—$R^{2a}$, *—$R^{2b}$—COO—$R^{2c}$, or *—$R^{2d}$—O—$R^{2e}$. $R^{2a}$ represents a substituted or unsubstituted monovalent fluorinated hydrocarbon group having 10 to 20 carbon atoms. $R^{2b}$ represents a substituted or unsubstituted divalent hydrocarbon group having 1 to 20 carbon atoms, a substituted or unsubstituted divalent fluorinated hydrocarbon group having 1 to 20 carbon atoms, or a divalent organic group having a lactone structure and having 4 to 20 carbon atoms. $R^{2c}$ represents a substituted or unsubstituted monovalent hydrocarbon group having 1 to 20 carbon atoms or a substituted or unsubstituted monovalent fluorinated hydrocarbon group having 1 to 20 carbon atoms, wherein at least one of $R^{2b}$ and $R^{2c}$ has a fluorine atom. $R^{2d}$ represents a substituted or unsubstituted divalent hydrocarbon group having 1 to 20 carbon atoms, a substituted or unsubstituted divalent fluorinated hydrocarbon group having 1 to 20 carbon atoms, or a divalent organic group having a lactone structure and having 4 to 20 carbon atoms. $R^{2e}$ represents a substituted or unsubstituted monovalent hydrocarbon group having 1 to 20 carbon atoms, a substituted or unsubstituted monovalent fluorinated hydrocarbon group having 1 to 20 carbon atoms, or —$R^{2f}$—O—$R^{2g}$. $R^{2f}$ represents a substituted or unsubstituted divalent hydrocarbon group having 1 to 20 carbon atoms or a substituted or unsubstituted divalent fluorinated hydrocarbon group having 1 to 20 carbon atoms. $R^{2g}$ represents a substituted or unsubstituted monovalent hydrocarbon group having 1 to 20 carbon atoms or a substituted or unsubstituted monovalent fluorinated hydrocarbon group having 1 to 20 carbon atoms, wherein at least one of $R^{2d}$ and $R^{2e}$ has a fluorine atom.

In the case in which the group defined as (1-2) is the substituted or unsubstituted monovalent fluorinated hydrocarbon group having 1 to 20 carbon atoms, the monovalent fluorinated hydrocarbon group may be exemplified by a group obtained by substituting with a fluorine atom, at least one hydrogen atom contained in groups similar to the monovalent hydrocarbon group having 1 to 20 atoms represented by $R^X$ in the above formula (2-1A), and the like.

In this case, the monovalent fluorinated hydrocarbon group is preferably a monovalent chain fluorinated hydrocarbon group having 1 to 6 carbon atoms or an aromatic fluorinated hydrocarbon group having 6 to 10 carbon atoms. Each substituent which may be included in the above groups is preferably —OH.

In the case in which the group defined as (1-2) is *—CO—$R^{2a}$, the monovalent fluorinated hydrocarbon group which may be represented by $R^{2a}$ may be exemplified by groups obtained by substituting with a fluorine atom, at least one hydrogen atom contained in groups similar to the monovalent hydrocarbon group represented by $R^X$ in the above formula (2-1A), and the like.

In this case, $R^{2a}$ represents preferably a substituted or unsubstituted monovalent chain fluorinated hydrocarbon group having 1 to 6 carbon atoms. The substituent which may be included in $R^{2a}$ is preferably —OH or —COO—$R^{2h}$. $R^{2h}$ represents a monovalent hydrocarbon group having 1 to 20 carbon atoms. The monovalent hydrocarbon group having 1 to 20 carbon atoms represented by $R^{2h}$ may be exemplified by groups similar to the monovalent hydrocarbon group represented by $R^X$ in the above formula (2-1A), and the like. $R^{2h}$ represents preferably a monovalent chain hydrocarbon group having 1 to 4 carbon atoms, or a monovalent alicyclic hydrocarbon group having 6 to 10 carbon atoms.

In the case in which the group defined as (1-2) is —$R^{2b}$—COO—$R^{2c}$, the divalent hydrocarbon group which may be represented by $R^{2b}$ may be exemplified by groups similar to the divalent hydrocarbon group in X, and the like. The divalent fluorinated hydrocarbon group which may be represented by $R^{2b}$ may be exemplified by groups obtained by substituting with a fluorine atom, at least one hydrogen atom contained in groups similar to the divalent hydrocarbon group which may be represented by X, and the like. The lactone structure which may be contained in $R^{2b}$ may be exemplified by structures represented by the above formulae (X-1) and (X-2), and the like. The monovalent fluorinated hydrocarbon group which may be represented by $R^{2c}$ may be exemplified by groups obtained by substituting with a fluorine atom, at least one hydrogen atom contained in the monovalent hydrocarbon group represented by $R^X$ in the above formula (2-1A), and the like.

In this case, $R^{2b}$ represents preferably a substituted or unsubstituted divalent chain fluorinated hydrocarbon group having 1 to 6 carbon atoms. $R^{2c}$ represents preferably a monovalent chain hydrocarbon group having 1 to 4 carbon atoms. The substituent which may be included in $R^{2b}$ is preferably —OH or —COO—$R^{2i}$. $R^{2i}$ represents a monovalent hydrocarbon group having 1 to 20 carbon atoms. The monovalent hydrocarbon group represented by $R^{2i}$ may be exemplified by groups similar to the monovalent hydrocarbon group represented by $R^X$ in the above formula (R-1A), and the like. $R^{2i}$ represents preferably a monovalent chain hydrocarbon group having 1 to 4 carbon atoms.

In the case in which the group defined as (1-2) is —$R^{2d}$—O—$R^{2e}$, the divalent hydrocarbon group which may be represented by $R^{2d}$ may be exemplified by groups similar to the divalent hydrocarbon group which may be represented by X, and the like. The divalent fluorinated hydrocarbon group which may be represented by $R^{2d}$ may be exemplified by groups obtained by substituting with a fluorine atom, at least one hydrogen atom contained in groups similar to the divalent hydrocarbon group which may be represented by X, and the like. The lactone structure which may be contained in $R^{2d}$ may be exemplified by the structures represented by the above formulae (X-1) and (X-2), and the like. The monovalent hydrocarbon group which may be represented by $R^{2e}$ may be exemplified by groups similar to the monovalent hydrocarbon group represented by $R^X$ in the above formula (2-1A), and the like. The monovalent fluorinated hydrocarbon group which may be represented by $R^{2e}$ may be exemplified by groups obtained by substituting with a fluorine atom, at least one hydrogen atom contained in the monovalent hydrocarbon group represented by $R^X$ in the above formula (2-1A), and the like. In the case in which $R^{2e}$ represents —$R^{2f}$—O—$R^{2g}$, the divalent hydrocarbon group which may be represented by $R^{2f}$ may be exemplified by groups similar to the divalent hydrocarbon group in X, and the like. The divalent fluorinated hydrocarbon group which may be represented by $R^{2f}$ may be exemplified by groups obtained by substituting with a fluorine atom, at least one hydrogen atom contained in groups similar to the divalent hydrocarbon group which may be represented by X, and the like. The monovalent hydrocarbon group which may be represented by $R^{2g}$ may be exemplified by groups similar to the monovalent hydrocarbon group represented by $R^X$ in the above formula (2-1A), and the like. The monovalent fluorinated hydrocarbon group which may be represented by $R^{2g}$ may be exemplified by groups obtained by substituting with a fluorine atom, at least one hydrogen atom contained in the monovalent hydrocarbon group represented by $R^X$ in the above formula (2-1A), and the like.

In this case, $R^{2d}$ represents preferably a substituted or unsubstituted divalent chain fluorinated hydrocarbon group having 1 to 4 carbon atoms. In the case in which $R^{2e}$ represents the substituted or unsubstituted monovalent hydrocarbon group having 1 to 20 carbon atoms, the monovalent hydrocarbon group which may be represented by $R^{2e}$ is preferably a monovalent chain hydrocarbon group having 1 to 4 carbon atoms. In the case in which $R^{2e}$ represents $—R^{2f}—O—R^{2g}$, the divalent hydrocarbon group which may be represented by $R^{2f}$ is preferably a divalent chain hydrocarbon group having 1 to 4 carbon atoms, and the monovalent hydrocarbon group which may be represented by $R^{2g}$ is preferably a monovalent chain hydrocarbon group having 1 to 4 carbon atoms. Each substituent which may be included in $R^{2d}$, $R^{2e}$, $R^{2f}$, and $R^{2g}$ is, preferably independently —OH.

Compound (F)

A monomer that gives the structural unit (T) may be exemplified by the compound (F) represented by the following formula (i), and the like.

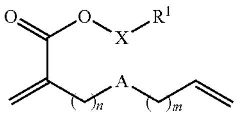

(i)

In the above formula (i), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group having a fluorine atom.

In the above formula (i), A, X, and $R^1$ are equivalent to A, X, and $R^1$ in the above formula (1).

The compound (F) is generated by a cyclization reaction during polymerization as shown below, and consequently, the structural unit (T) is formed.

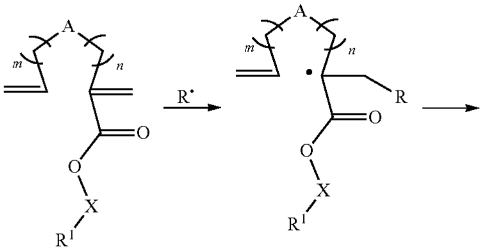

-continued

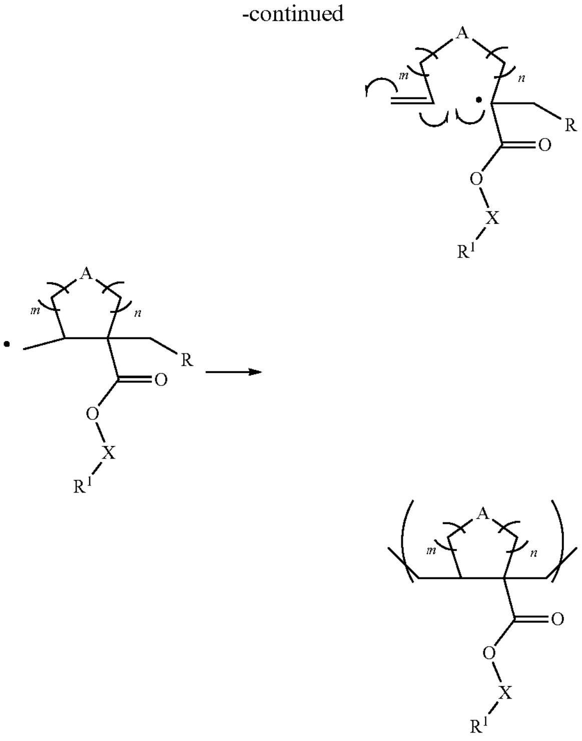

Of specific examples of the compound (F), compounds represented by the following formulae may be exemplified as specific examples of a compound in which $R^1$ represents the group defined as (1-1).

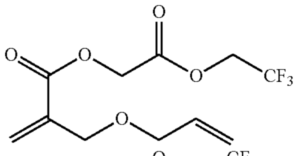

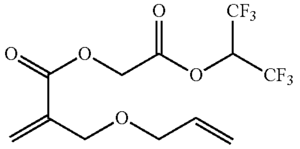

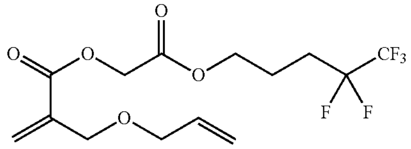

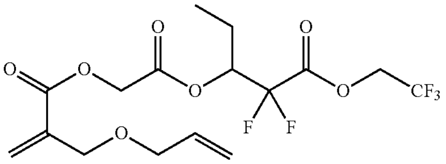

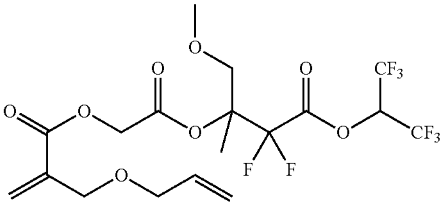

-continued
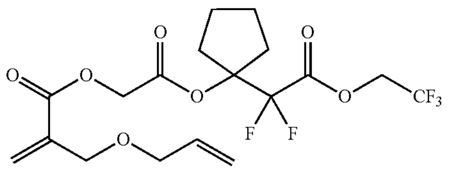
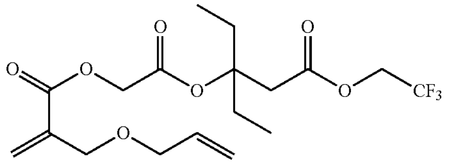
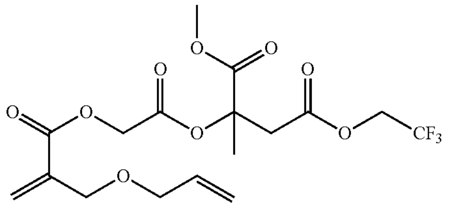
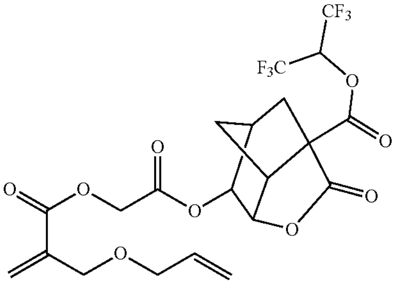
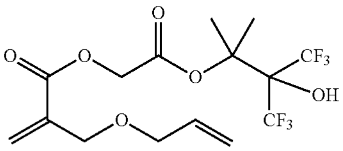
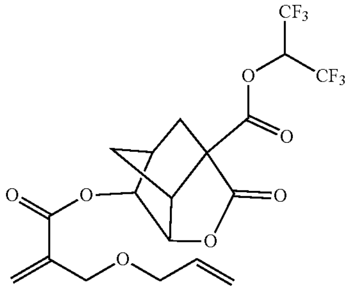
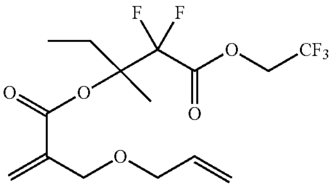
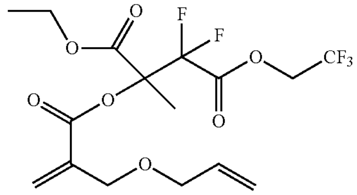
-continued
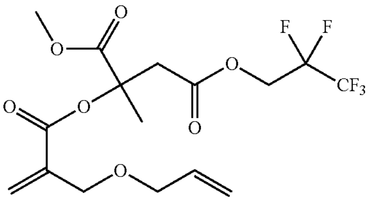
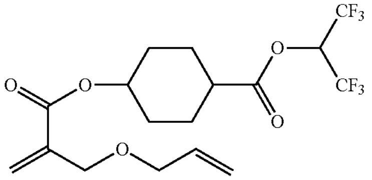
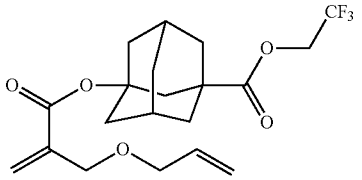
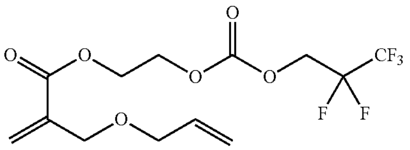
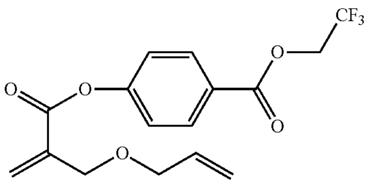
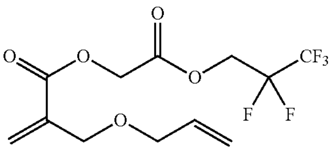
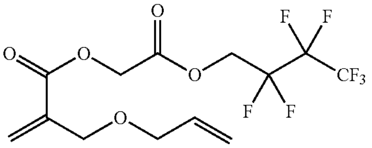
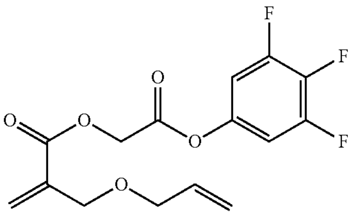
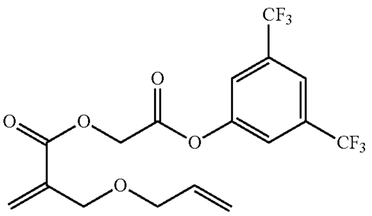

-continued
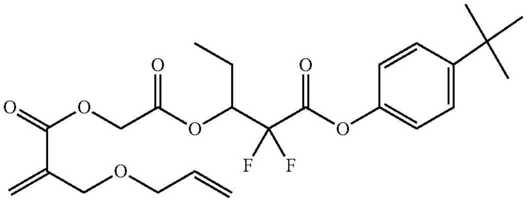
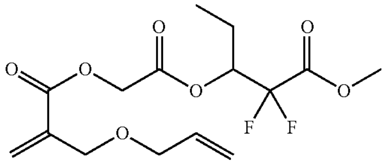
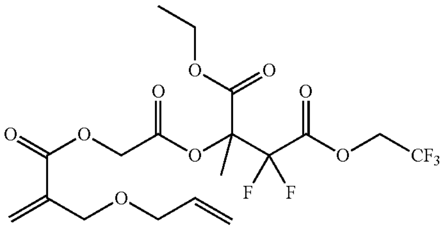
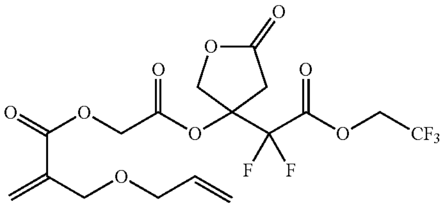
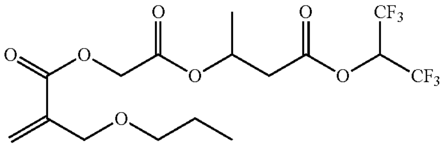
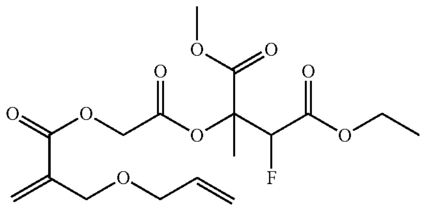
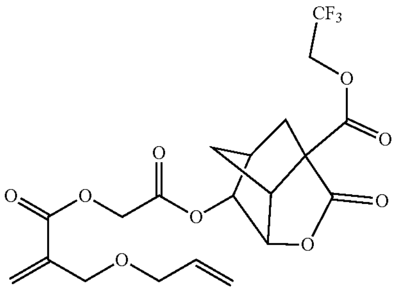
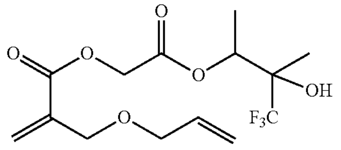
-continued
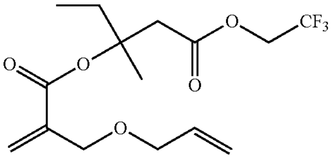
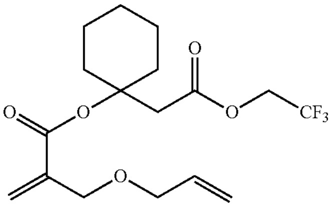
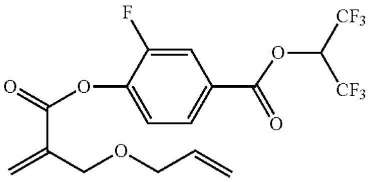
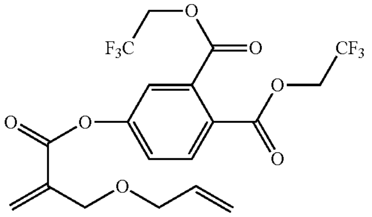 [SMILES: C=CCOCC(=C)C(=O)Oc1ccc(C(=O)OCC(F)(F)F)c(C(=O)OCC(F)(F)F)c1]
Of specific examples of the compound (F), compounds represented by the following formulae can be exemplified as specific examples of a compound in which $R^1$ represents the group defined as (1-2).
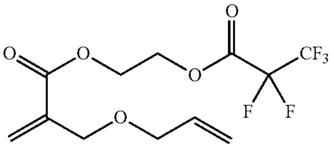
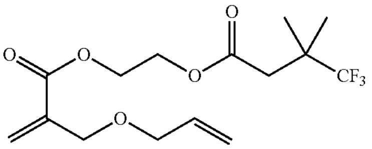
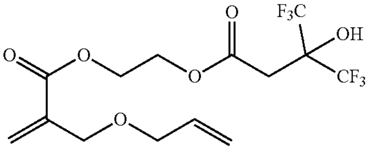
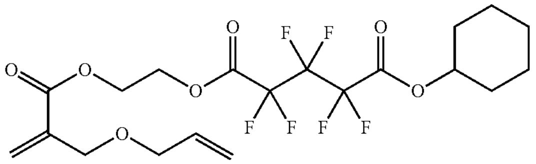
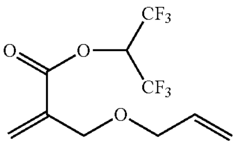

-continued

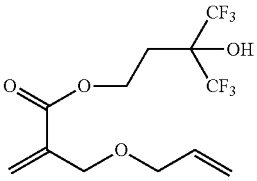

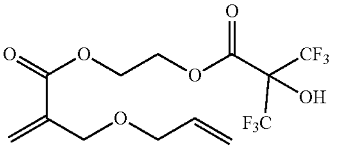

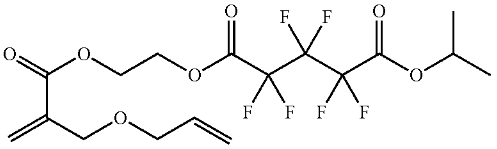

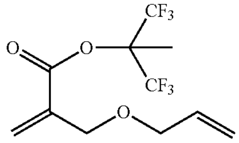

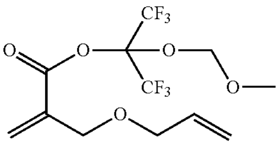

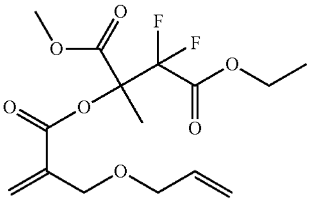

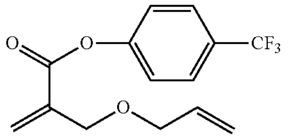

Examples of the structural unit (T) include structural units derived from, as monomers, the compounds described above, and the like.

The lower limit of a proportion of the structural unit (T) with respect to total structural units constituting the polymer (A) is preferably 1 mol %, more preferably 5 mol %, still more preferably 20 mol %, and particularly preferably 40 mol %. The upper limit of the proportion is preferably 99 mol %, more preferably 95 mol %, and still more preferably 90 mol %. When the proportion of the structural unit (T) falls within the above range, the sensitivity of the radiation-sensitive resin composition to exposure light can be further improved, and moreover, the highly water repellent property and the defect-inhibiting property can be further improved.

Structural Unit (F)

Examples of the structural unit (F) include a structural unit represented by the following formula (f-1), and the like.

(f-1)

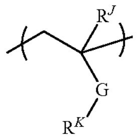

In the above formula (f-1), $R^J$ represents a hydrogen atom, a fluorine atom, a methyl group, or a trifluoromethyl group; G represents a single bond, an oxygen atom, a sulfur atom, —COO—, —$SO_2$—NH—, —CONH—, or —OCONH—; and $R^K$ represents a monovalent organic group having 1 to 8 carbon atoms which has a fluorine atom.

In light of copolymerizability of a monomer that gives the structural unit (F), $R^J$ represents preferably a hydrogen atom or a methyl group, and more preferably a methyl group. G represents preferably —COO—, —$SO_2$NH—, —CONH—, or —OCONH—, and more preferably —COO—.

Examples of the structural unit (F) include structural units derived from, as monomers, compounds represented by the formulae (m-14) to (m-19) and (m-21) to (m-23) disclosed in EXAMPLES, described later, and the like.

The lower limit of a proportion of the structural unit (F) with respect to total structural units constituting the polymer (E) is preferably 1 mol %, more preferably 5 mol %, and still more preferably 10 mol %. The upper limit of the proportion is preferably 90 mol %, more preferably 80 mol %, and still more preferably 70 mol %. When the proportion of the structural unit (F) falls within the above range, the proportion by mass of fluorine atoms contained in the polymer (E) can be still more appropriately adjusted.

The polymer (E) preferably has a structural unit including an acid-labile group and/or a structural unit including an alcoholic hydroxyl group. The structural unit including the acid-labile group is exemplified by the structural units exemplified as the structural unit (I) in the polymer (A), and the like. The structural unit including the alcoholic hydroxyl group is exemplified by the structural units exemplified as the structural unit (III) in the polymer (A), and the like.

The lower limit of a proportion of the structural unit including the acid-labile group with respect to total structural units constituting the polymer (E) is preferably 1 mol %, and more preferably 5 mol %. The upper limit of the proportion is preferably 70 mol %, more preferably 60 mol %, and still more preferably 50 mol %.

The lower limit of a proportion of the structural unit including the alcoholic hydroxyl group with respect to total structural units constituting the polymer (E) is preferably 1 mol %, and more preferably 5 mol %. The upper limit of the proportion is preferably 60 mol %, more preferably 50 mol %, and still more preferably 40 mol %.

Other Structural Unit(s)

The polymer (E) may have the other structural unit(s) within a range not leading to impairment of the effects of the present invention. The proportion of the other structural unit(s) may be appropriately determined in accordance with a purpose thereof.

The lower limit of a polystyrene-equivalent weight average molecular weight (Mw) of the polymer (E) as determined by gel permeation chromatography (GPC) is preferably 2,000, more preferably 3,000, still more preferably 4,000, and particularly preferably 5,000. The upper limit of the Mw is preferably 30,000, more preferably 20,000, still more preferably 15,000, and particularly preferably 10,000. When the Mw of the polymer (E) falls within the above range, coating characteristics of the radiation-sensitive resin composition can be improved, and as a result, the LWR performance and the CDU performance can be further improved.

The upper limit of a ratio (Mw/Mn) of the Mw to a polystyrene-equivalent number average molecular weight (Mn) of the polymer (E) as determined by GPC is preferably 3.00, more preferably 2.50, still more preferably 2.00, and particularly preferably 1.85. The lower limit of the ratio is typically 1.00, and preferably 1.10.

The lower limit of a content of the polymer (E) with respect to 100 parts by mass of the polymer (A) is preferably 0.1 parts by mass, more preferably 0.5 parts by mass, and still more preferably 1 part by mass. The upper limit of the content is preferably 30 parts by mass, more preferably 25 parts by mass, and still more preferably 20 parts by mass. The radiation-sensitive resin composition may contain one, or two or more types of the polymer (E).

Method of Synthesizing Polymer (E)

The polymer (E) can be synthesized by, for example, polymerizing a monomer that gives each structural unit in accordance with a well-known procedure.

(B) Acid Generator

The acid generator (B) is a component which generates an acid by irradiation with a radioactive ray. Examples of the radioactive ray include electromagnetic waves such as a visible light ray, an ultraviolet ray, a far ultraviolet ray, EUV, an X-ray, and a γ-ray; charged particle rays such as an electron beam and an α-ray, and the like. A change in solubility in a developer solution and the like of the polymer (A) in the radiation-sensitive resin composition is promoted by an action of the acid generated from the acid generator (B), and as a result, the resolution and the LWR performance can be further improved. The acid generator (B) may be contained in the radiation-sensitive resin composition either in the form of a low-molecular-weight compound (hereinafter, may be also referred to as "(B) acid generating agent" or "acid generating agent (B)") or in the form of an acid generator incorporated as a part of a polymer such as the polymer (A) or the like, or may be in a combination of both these forms.

The acid generating agent (B) is exemplified by an onium salt compound, an N-sulfonyloxyimide compound, a halogen-containing compound, a diazoketone compound, and the like.

Examples of the onium salt compound include a sulfonium salt, a tetrahydrothiophenium salt, an iodonium salt, a phosphonium salt, a diazonium salt, a pyridinium salt, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium camphorsulfonate, 4-cyclohexylphenyldiphenylsulfonium nonafluoro-n-butanesulfonate, 4-methanesulfonylphenyldiphenylsulfonium nonafluoro-n-butanesulfonate, triphenylsulfonium 1,1,2,2-tetrafluoro-6-(1-adamantanecarbonyloxy)-hexane-1-sulfonate (a compound represented by the formula (B-4) in EXAMPLES, described later), triphenylsulfonium 2-(1-adamantyl)-1,1-difluoroethanesulfonate, triphenylsulfonium 2-(adamantane-1-ylcarbonyloxy)-1,1,3,3,3-pentafluoropropane-1-sulfonate (a compound represented by the formula (B-3) in EXAMPLES, described later), triphenylsulfonium maleate, and the like. Other examples of the sulfonium salt include compounds represented by the formulae (B-1), (B-5), and (B-6) in EXAMPLES, described later, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl) tetrahydrothiophenium 2-bicyclo[2.2.1]hept-2-yl-1,1,2,2-tetrafluoroethanesulfonate (a compound represented by formula (B-2) in EXAMPLES, described later), 1-(4-n-butoxynaphthalen-1-yl)tetrahydrothiophenium camphorsulfonate, 1-(6-n-butoxynaphthalen-2-yl)tetrahydrothiophenium nonafluoro-n-butanesulfonate, 1-(3,5-dimethyl-4-hydroxyphenyl)tetrahydrothiophenium nonafluoro-n-butanesulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, diphenyliodonium camphorsulfonate, bis(4-t-butylphenyl)iodonium nonafluoro-n-butanesulfonate, and the like.

Examples of the N-sulfonyloxyimide compound include N-trifluoromethylsulfonyloxy phthalimide, N-(trifluoromethylsulfonyloxy)-1,8-naphthalimide, N-(trifluoromethylsulfonyloxy)bicyclo[2.2.1]hept-5-ene-2,3-dicarboxyimide, N-(nonafluoro-n-butylsulfonyloxy)bicyclo[2.2.1]hept-5-ene-2,3-dicarboxyimide, N-(perfluoro-n-octylsulfonyloxy)-1,8-naphthalimide, N-(perfluoro-n-octylsulfonyloxy)bicyclo[2.2.1]hept-5-ene-2,3-dicarboxyimide, N-(2-bicyclo[2.2.1]hept-2-yl-1,1,2,2-tetrafluoroethylsulfonyloxy) bicyclo[2.2.1]hept-5-ene-2,3-dicarboxyimide, N-(2-(3-tetracyclo[4.4.0.$1^{2,5}$.$1^{7,10}$]dodecanyl)-1,1-difluoroethylsulfonyloxy)bicyclo[2.2.1]hept-5-ene-2,3-dicarboxyimide, N-(camphorsulfonyloxy)bicyclo[2.2.1]hept-5-ene-2,3-dicarboxyimide, and the like.

Of these, the acid generating agent (B) is preferably the sulfonium salt or the tetrahydrothiophenium salt, and more preferably a compound represent by the following formulae (B-1) to (B-6). Other examples of the acid generating agent (B) include compounds exemplified as the acid generator (B) in Japanese Unexamined Patent Application, Publication No. 2018-013744, and the like.

In the case in which the acid generator (B) is the acid generating agent (B), the lower limit of a content of the acid generating agent (B) with respect to 100 parts by mass of the polymer (A) is preferably 0.1 parts by mass, more preferably 1 part by mass, still more preferably 2 parts by mass, and particularly preferably 5 parts by mass. The upper limit of the content is preferably 100 parts by mass, more preferably 60 parts by mass, still more preferably 40 parts by mass, and particularly preferably 30 parts by mass. When the content of the acid generating agent (B) falls within the above range, the sensitivity of the radiation-sensitive resin composition to exposure light can be further improved, and moreover, the highly water repellent property and the defect-inhibiting property can be further improved. The radiation-sensitive resin composition may contain one, or two or more types of the acid generator (B).

Furthermore, the acid generator (B) may be exemplified by a polymer in which the structure of the acid generator is incorporated as a part of a polymer such as the polymer (A).

(C) Acid Diffusion Controller

The radiation-sensitive resin composition may contain the acid diffusion controller (C) as an optional component. The acid diffusion controller (C) controls a diffusion phenomenon, in the resist film, of the acid generated from the acid generating agent (B) and the like upon exposure, thereby achieving an effect of controlling unwanted chemical reactions in a light-unexposed region. The acid diffusion controller (C) may be contained in the radiation-sensitive resin composition in the form of a low-molecular weight compound (hereinafter, may be also appropriately referred to as "(C) acid diffusion control agent" or "acid diffusion control agent (C)") or in the form of an acid diffusion controller incorporated as a part of a polymer such as the polymer (A) or the like, or may be in a combination of both these forms.

The acid diffusion control agent (C) is exemplified by a photodegradable base that is photosensitized by an exposure to generate a weak acid, and the like. An exemplary photodegradable base includes a compound containing a radiation-sensitive onium cation which degrades upon exposure and an anion of a weak acid, and the like. In a light-exposed region, the photodegradable base generates a weak acid from: a proton generated upon degradation of the radiation-sensitive onium cation; and the anion of the weak acid, whereby acid diffusion controllability decreases. Examples of the photodegradable base include compounds represented by the formulae (C-1) to (C-4) disclosed in EXAMPLES, described later, and the like. Alternatively, the acid diffusion control agent (C) is exemplified by a nitrogen-containing compound. Specific examples of the nitrogen-containing compound include a compound represented by the formula (C-5) disclosed in EXAMPLES, described later, and the like. Specific examples of the acid diffusion control agent (C) other than the photodegradable base and the nitrogen-containing compound include compounds exemplified as the acid diffusion control agent (D) in Japanese Unexamined Patent Application, Publication No. 2018-013744.

In the case in which the radiation-sensitive resin composition contains the acid diffusion control agent (C), the lower limit of a content of the acid diffusion control agent (C) with respect to 100 parts by mass of the polymer (A) is preferably 0.1 parts by mass, more preferably 0.5 parts by mass, and still more preferably 1 part by mass. The upper limit of the content is preferably 20 parts by mass, more preferably 10 parts by mass, and still more preferably 5 parts by mass.

The lower limit of a proportion of the acid diffusion control agent (C) with respect to 100 mol % of the acid generating agent (B) is preferably 1 mol %, more preferably 5 mol %, and still more preferably 10 mol %. The upper limit of the proportion is preferably 250 mol %, more preferably 150 mol %, and still more preferably 100 mol %.

When the content and the proportion of the acid diffusion control agent (C) fall within the above ranges, the sensitivity of the radiation-sensitive resin composition to exposure light, the highly water repellent property, and the defect-inhibiting property can be further improved. The radiation-sensitive resin composition may contain one, or two or more types of the acid diffusion controller (C).

(D) Solvent

The radiation-sensitive resin composition typically contains the solvent (D). The solvent (D) is not particularly limited as long as it is a solvent capable of dissolving or dispersing at least the polymer (A), the polymer (E), the acid generator (B), and the optional component(s), which is/are contained as desired.

The solvent (D) is exemplified by an alcohol solvent, an ether solvent, a ketone solvent, an amide solvent, an ester solvent, a hydrocarbon solvent, and the like.

Examples of the alcohol solvent include:

aliphatic monohydric alcohol solvents having 1 to 18 carbon atoms such as 4-methyl-2-pentanol;

alicyclic monohydric alcohol solvents having 3 to 18 carbon atoms such as cyclohexanol;

polyhydric alcohol solvents having 2 to 18 carbon atoms such as 1,2-propylene glycol;

polyhydric alcohol partial ether solvents having 3 to 19 carbon atoms such as propylene glycol-1-monomethyl ether; and the like.

Examples of the ether solvent include:

dialkyl ether solvents such as diethyl ether;

cyclic ether solvents such as tetrahydrofuran;

aromatic ring-containing ether solvents such as diphenyl ether; and the like.

Examples of the ketone solvent include:

chain ketone solvents such as acetone;

cyclic ketone solvents such as cyclohexanone;

2,4-pentanedione, acetonylacetone, and acetophenone; and the like.

Examples of the amide solvent include:

cyclic amide solvents such as N,N'-dimethylimidazolidinone;

chain amide solvents such as N-methylformamide; and the like.

Examples of the ester solvent include:

monocarboxylic acid ester solvents such as ethyl lactate;

polyhydric alcohol carboxylate solvents such as propylene glycol acetate;

polyhydric alcohol partial ether carboxylate solvents such as propylene glycol monomethyl ether acetate;

polyhydric carboxylic acid diester solvents such as diethyl oxalate;

lactone solvents such as γ-butyrolactone;

carbonate solvents such as dimethyl carbonate; and the like.

Examples of the hydrocarbon solvent include:

aliphatic hydrocarbon solvents having 5 to 12 carbon atoms such as n-pentane;

aromatic hydrocarbon solvents having 6 to 16 carbon atoms such as toluene; and the like.

Of these, the ketone solvent or the ester solvent is preferred; the cyclic ketone solvent, the monocarboxylic acid ester solvent, the polyhydric alcohol partial ether carboxylate solvent, or the lactone solvent is more preferred; and cyclohexanone, ethyl lactate, propylene glycol monomethyl ether acetate, or γ-butyrolactone is still more preferred. The radiation-sensitive resin composition may contain one, or two or more types of the solvent (D).

The lower limit of a proportion of the solvent (D) in the radiation-sensitive resin composition is preferably 50% by mass, more preferably 60% by mass, and still more preferably 70% by mass. The upper limit of the proportion is preferably 99.9% by mass, more preferably 99.5% by mass, and still more preferably 99% by mass.

The lower limit of a content of the solvent (D) with respect to 100 parts by mass of the polymer (A) is preferably 100 parts by mass, more preferably 500 parts by mass, and still more preferably 1,000 parts by mass. The upper limit of the content is preferably 20,000 parts by mass, more preferably 15,000 parts by mass, and still more preferably 10,000 parts by mass.

Other Optional Component(s)

Examples of the other optional component(s) include a surfactant, and the like. The radiation-sensitive resin composition may contain one, or two or more types of the other optional component(s).

Method of Preparing Radiation-Sensitive Resin Composition

The radiation-sensitive resin composition may be prepared, for example, by mixing the polymer (A), the polymer (E), and the acid generator (B), as well as the optional components such as the acid diffusion controller (C), the solvent (D), and the like, which are added as needed, in a certain ratio, and preferably filtering a thus resulting mixture through a membrane filter having a pore size of no greater than 0.2 μm.

The radiation-sensitive resin composition may be used either for positive-tone pattern formation conducted using an alkaline developer solution, or for negative-tone pattern formation conducted using an organic solvent-containing developer solution. The radiation-sensitive resin composition may be suitably used for ArF exposure, involving exposure with an ArF excimer laser beam, or for EUV exposure, involving exposure with an extreme ultraviolet ray (EUV).

Method of Forming Resist Pattern

The method of forming a resist pattern according to another embodiment of the present invention includes: a step (hereinafter, may be also referred to as "applying step") of applying the radiation-sensitive resin composition of the one embodiment of the invention directly or indirectly on a substrate; a step (hereinafter, may be also referred to as "exposing step") of exposing a resist film formed by the applying step; and a step (hereinafter, may be also referred to as "developing step") of developing the resist film exposed.

Due to using the radiation-sensitive resin composition according to the one embodiment of the present invention, the method of forming a resist pattern of the other embodiment of the present invention enables formation of a resist pattern with favorable sensitivity to exposure light, and having superior water repellency and few defects. Each step will be described below.

Applying Step

In this step, the radiation-sensitive resin composition is applied directly or indirectly on a substrate. Accordingly, a resist film is formed. The substrate is exemplified by a conventionally well-known substrate such as a silicon wafer, a wafer coated with silicon dioxide or aluminum, and the like. In addition, an organic or inorganic antireflective film disclosed in, for example, Japanese Examined Patent Application, Publication No. H6-12452, Japanese Unexamined Patent Application, Publication No. S59-93448, or the like may be provided on the substrate. An application procedure is exemplified by spin-coating, cast coating, roll-coating, and the like. After the application, prebaking (PB) may be carried out as needed for evaporating the solvent remaining in the coating film. The lower limit of a PB temperature is preferably 60° C., and more preferably 80° C. The upper limit of the PB temperature is preferably 150° C., and more preferably 140° C. The lower limit of a PB time period is preferably 5 sec, and more preferably 10 sec. The upper limit of the PB time period is preferably 600 sec, and more preferably 300 sec. The lower limit of an average thickness of the resist film formed is preferably 10 nm, and more preferably 20 nm. The upper limit of the average thickness is preferably 1,000 nm, and more preferably 500 nm.

Exposing Step

In this step, the resist film formed by the applying step is exposed. This exposure is carried out by irradiation with an exposure light through a photomask (as the case may be, through a liquid immersion medium such as water). Examples of the exposure light include electromagnetic waves such as visible light rays, ultraviolet rays, far ultraviolet rays, EUV (13.5 nm), X-rays, and γ-rays; charged particle rays such as electron beams and α-rays; and the like, which may be selected in accordance with a line width and the like of the intended pattern. Of these, far ultraviolet rays, EUV, or electron beams are preferred; an ArF excimer laser beam (wavelength: 193 nm), a KrF excimer laser beam (wavelength: 248 nm), EUV, or an electron beam is more preferred; and an ArF excimer laser beam or EUV is still more preferred. It is to be noted that exposure conditions such as exposure dose and the like may be appropriately selected in accordance with a formulation of the radiation-sensitive resin composition, type(s) of additive(s), the type of exposure light, and the like.

It is preferred that post exposure baking (PEB) is carried out after the exposure to promote dissociation of the acid-labile group included in the polymer (A) caused by the acid generated upon the exposure in exposed regions of the resist film. This PEB enables an increase in a difference in solubility of the resist film in a developer solution between the light-exposed regions and light-unexposed regions. The lower limit of a PEB temperature is preferably 50° C., more preferably 80° C., and still more preferably 90° C. The upper limit of the PEB temperature is preferably 180° C., and more preferably 130° C. The lower limit of a PEB time period is preferably 5 sec, more preferably 10 sec, and still more preferably 30 sec. The upper limit of the PEB time period is preferably 600 sec, more preferably 300 sec, and still more preferably 100 sec.

Developing Step

In this step, the resist film exposed is developed. Accordingly, formation of a predetermined resist pattern is enabled. The development is typically followed by washing with a rinse agent such as water or an alcohol and then drying. The development procedure in the developing step may be carried out by either development with an alkali, using an alkaline developer solution, or development with an organic solvent, using an organic solvent-containing developer solution.

In the case of the development with an alkali, the alkaline developer solution for use in the development is exemplified by: alkaline aqueous solutions prepared by dissolving at least one alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene, and 1,5-diazabicyclo-[4.3.0]-5-nonene; and the like. Of these, an aqueous TMAH solution is preferred, and a 2.38% by mass aqueous TMAH solution is more preferred.

In the case of the development with an organic solvent, the organic solvent-containing developer solution is exemplified by: an organic solvent such as an alcohol solvent, an ether solvent, a ketone solvent, an ester solvent, and a hydrocarbon solvent; a solvent containing the organic solvent; and the like. An exemplary organic solvent includes one, or two or more types of the solvents exemplified as the solvent (D), described above, and the like. Of these, the ester solvent or the ketone solvent is preferred. The ester solvent is preferably an acetic acid ester solvent, and more preferably n-butyl acetate. The ketone solvent is preferably the chain ketone, and more preferably 2-heptanone. The lower limit of a proportion of the organic solvent in the developer solution is preferably 80% by mass, more preferably 90% by mass, still more preferably 95% by mass, and particularly preferably 99% by mass. Examples of components other than the organic solvent in the developer solution are exemplified by water, silicone oil, and the like.

Examples of the development procedure include: a dipping procedure in which the substrate is immersed for a given time period in the developer solution charged in a container; a puddle procedure in which the developer solution is placed to form a dome-shaped bead by way of the surface tension on the surface of the substrate for a given time period to conduct a development; a spraying procedure in which the developer solution is sprayed onto the surface of the substrate; a dynamic dispensing procedure in which the developer solution is continuously applied onto the substrate, which is rotated at a constant speed, while scanning with a developer solution-application nozzle at a constant speed; and the like.

The resist pattern to be formed according to the method of forming a resist pattern is exemplified by a line-and-space pattern, a hole pattern, and the like.

Polymer

The polymer of still another embodiment of the present invention is the polymer (E) having the structural unit (T) represented by the above formula (1). The polymer can be suitably used as a component of the radiation-sensitive resin composition of the one embodiment of the present invention, described above. The polymer is described as the polymer (E), described above.

Compound

The compound of yet another embodiment of the present invention is the compound (F) represented by the above formula (i). The compound is described as the compound (F), described above.

EXAMPLES

Hereinafter, the present invention is explained in detail by way of Examples, but the present invention is not in any way limited to these Examples. Measuring methods for various types of physical property values are shown below.

Weight Average Molecular Weight (Mw) and Number Average Molecular Weight (Mn)

Measurements of the Mw and the Mn of the polymer were carried out by gel permeation chromatography (GPC) using GPC columns available from Tosoh Corporation ("G2000 HXL"×2, "G3000 HXL"×1, and "G4000 HXL"×1) under the following conditions. Furthermore, a dispersity index (Mw/Mn) was calculated according to measurement results of the Mw and the Mn.

elution solvent: tetrahydrofuran
flow rate: 1.0 mL/min
sample concentration: 1.0% by mass
amount of injected sample: 100 uL
column temperature: 40° C.
detector: differential refractometer
standard substance: mono-dispersed polystyrene $^{13}C$-NMR Analysis A $^{13}C$-NMR analysis was performed using a nuclear magnetic resonance apparatus ("JNM-Delta 400," available from JEOL, Ltd.).

Synthesis of Compound (F) (Monomer)

Synthesis Example 1: Synthesis of Compound (F-1

Into a reaction vessel were charged 20.0 mml of ethyl 2-(bromomethyl)acrylate, 30.0 mmol of allyl alcohol, 40.0 mml of triethylamine, and 50 g of ethyl acetate, and a resulting mixture was stirred at 60° C. for 3 hrs. Thereafter, the reaction solution was cooled to no greater than 30° C. and water was added for dilution. Next, ethyl acetate was added and extraction was performed, whereby an organic layer was separated. The organic layer thus obtained was washed with a saturated aqueous sodium chloride solution, and then with water. After drying over sodium sulfate, a solvent was distilled away. Purification was carried out with column chromatography to give an alkoxy derivative with a favorable yield.

To the above-described alkoxy derivative was added a mixture of methanol:water (1:1 (mass ratio)) to give a 1 M solvent, and then 18.5 mmol of sodium hydroxide was added thereto, and a reaction was permitted at 50° C. for 4 hrs. Subsequently, the reaction solution was cooled to no greater than 30° C. and 1 M hydrochloric acid was added to acidify the system. Ethyl acetate was added and extraction was performed, whereby an organic layer was separated. The organic layer thus obtained was washed with a saturated aqueous sodium chloride solution, and then with water. After drying over sodium sulfate, a solvent was distilled away to give a carboxylic acid derivative with a favorable yield.

To the above-described carboxylic acid derivative were added 20.0 mml of 2,2,2-trifluoromethyl-2-bromoacetate, 40.0 mmol of cesium carbonate, and 50 g of dimethyl formamide, and a resulting mixture was stirred at 120° C. for 10 hrs. Subsequently, the reaction solution was cooled to no greater than 30° C. and water was added for dilution. Ethyl acetate was added and extraction was performed, whereby an organic layer was separated. The organic layer thus obtained was washed with a saturated aqueous sodium chloride solution, and then with water. After drying over sodium sulfate, a solvent was distilled away, and purification was carried out with column chromatography to give a compound represented by the following formula (F-1) (hereinafter, may be also referred to as "compound (F-1)" or "monomer (F-1)") with a favorable yield. A synthesis scheme of the compound (F-1) is shown below.

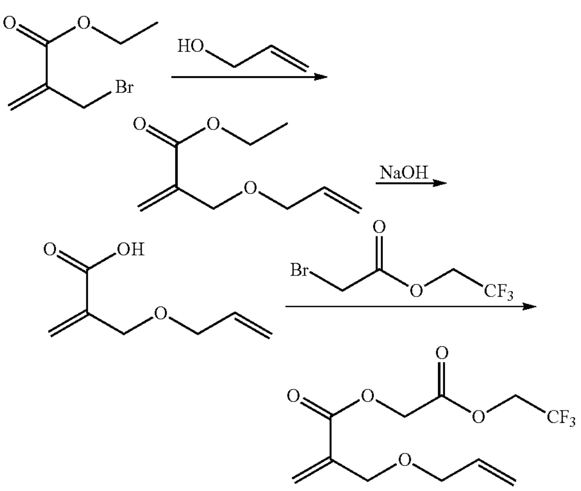

(F-1)

Synthesis Examples 2 to 10: Synthesis of Monomer (F-2) to Monomer (F-10

Compounds represented by the following formulae (F-2) to (F-10) were synthesized by an operation similar to that of Synthesis Example 1, except that instead of 2,2,2-trifluoromethyl-2-bromoacetate in Synthesis Example 1, corresponding materials were used. Hereinafter, compounds represented by the formulae (F-2) to (F-10) may be referred to as "compound (F-2)" to "(compound (F-10)" or "monomer (F-2)" to "monomer (F-10)".

(F-2)

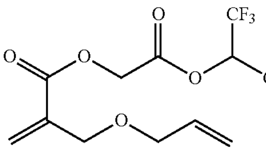

(F-3)

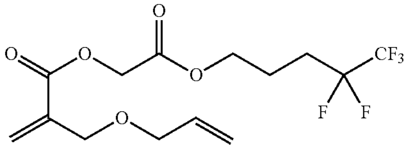

(F-4)

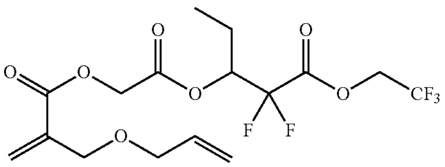

(F-5)

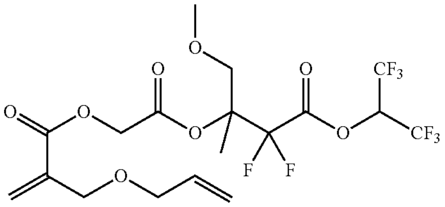

(F-6)

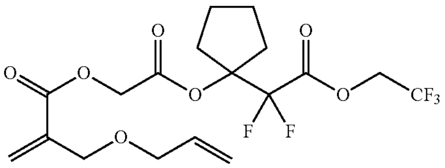

(F-7)

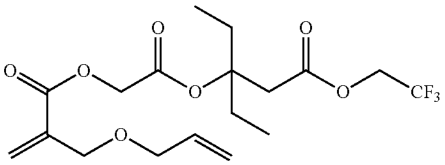

(F-8)

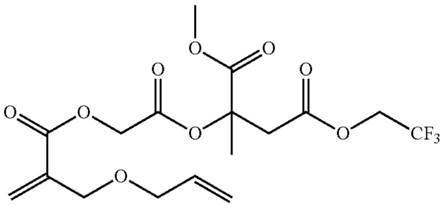

-continued (F-9)

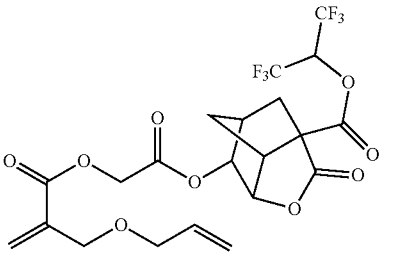

(F-10)

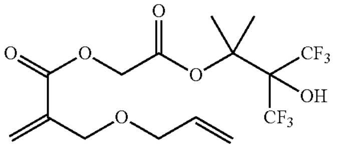

Synthesis Example 11: Synthesis of Compound (F-11

To the carboxylic acid derivative obtained in Synthesis Example 1 were added 30.0 mmol of 1-(3-dimethylamino-propyl)-3-ethylcarbodiimide hydrochloride, 3.0 mmol of 4-dimethylaminopyridine, 30.0 mml of 2-hydroxyethyl-2,2,3,3,3-pentafluoropropanate, and 50 g of dichloromethane, and a resulting mixture was stirred at 50° C. for 24 hrs. Next, the reaction solution was cooled to no greater than 30° C., and water was added for dilution. Dichloromethane was added thereto to perform extraction, whereby an organic layer was separated. The organic layer thus obtained was washed with a saturated aqueous sodium chloride solution, and then with water. After drying over sodium sulfate, a solvent was distilled away, and purification was carried out with column chromatography to give a compound represented by the following formula (F-11) (hereinafter, may be also referred to as "compound (F-11)" or "monomer (F-11)") with a favorable yield. A synthesis scheme of the compound (F-11) is shown below.

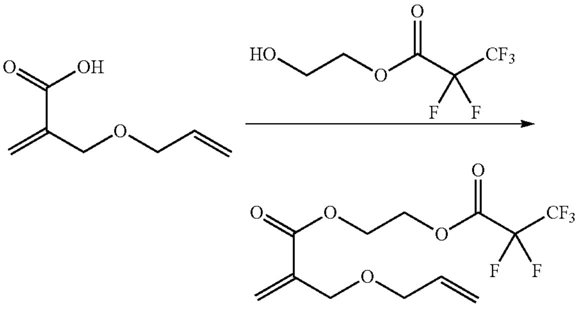

(F-11)

Synthesis Examples 12 to 24: Synthesis of Monomer (F-12) to Monomer (F-24

Compounds represented by the following formulae (F-12) to (F-24) were synthesized by an operation similar to that of Synthesis Example 11, except that instead of the 2-hydroxy-ethyl-2,2,3,3,3-pentafluoropropanate in Synthesis Example 11, corresponding materials were used. Hereinafter, compounds represented by the formulae (F-12) to (F-24) may be referred to as "compound (F-12)" to "compound (F-24)" or "monomer (F-12)" to "monomer (F-24)".

(F-12)

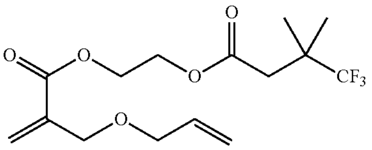

(F-13)

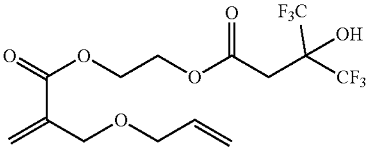

(F-14)

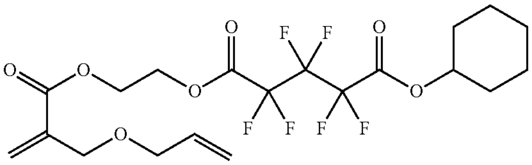

(F-15)

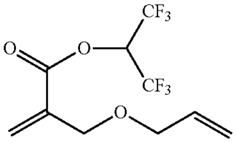

(F-16)

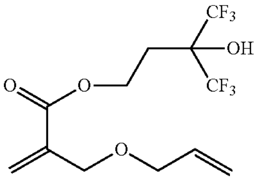

(F-17)

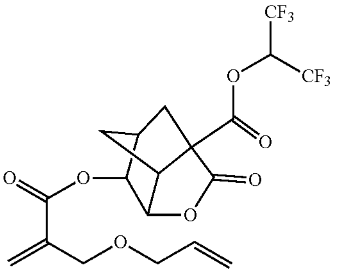

(F-18)

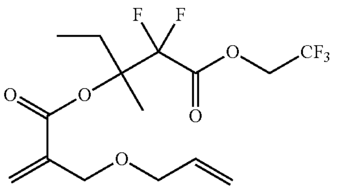

(F-19)

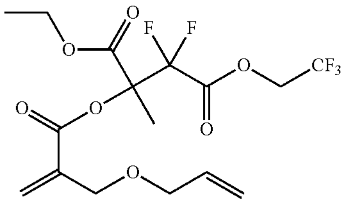

-continued (F-20)

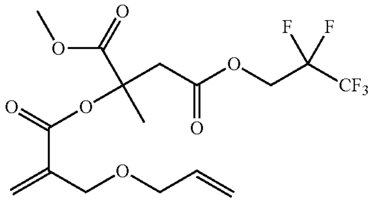

(F-21)

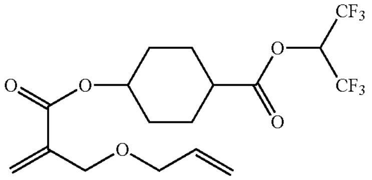

(F-22)

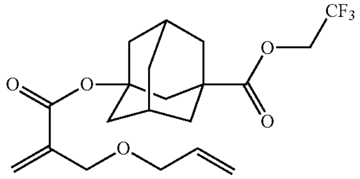

(F-23)

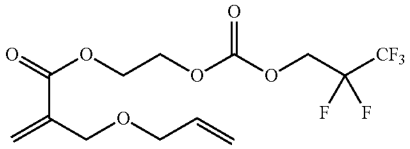

(F-24)

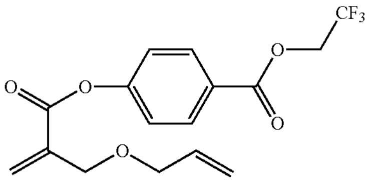

Synthesis of Polymer (A) and Polymer (E)

Of the monomers used for synthesizing each polymer in the Examples and the Comparative Examples, monomers other than the monomers (F-1) to (F-24) are shown below. It is to be noted that in the following Synthesis Examples, unless otherwise specified particularly, the term "parts by mass" means a value, provided that the total mass of the monomers used was 100 parts by mass, and the term "mol %" means a value, provided that the total mol number of the monomers used was 100 mol %.

(m-1)

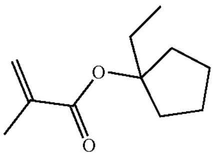

-continued
(m-2)
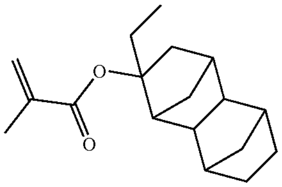
(m-3)
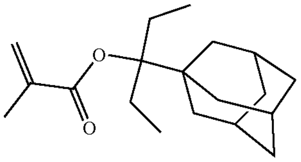
(m-4)
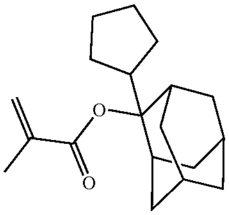
(m-5)
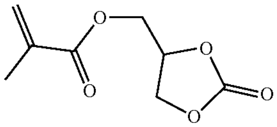
(m-6)
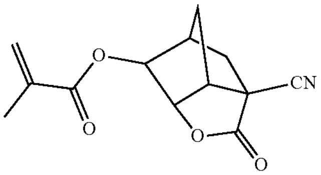
(m-7)
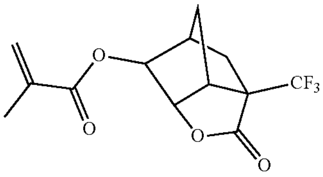
(m-8)
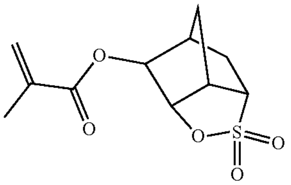
(m-9)
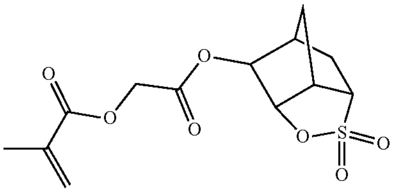
-continued
(m-10)
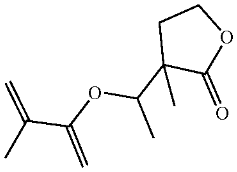
(m-11)
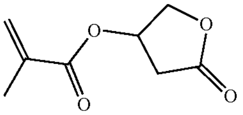
(m-12)
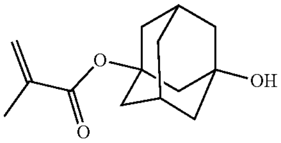
(m-13)
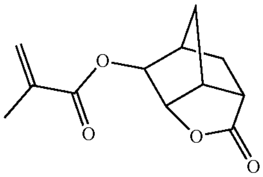
(m-14)
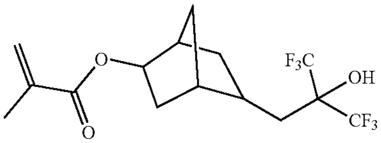
(m-15)
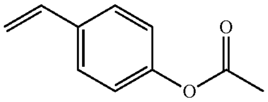
(m-16)
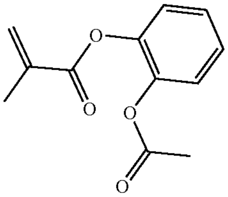
(m-17)
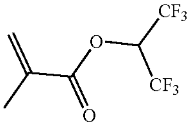
(m-18)
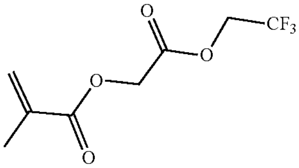
(m-19)
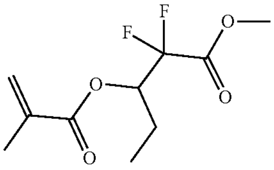

-continued (m-20)

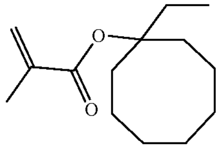

(m-21)

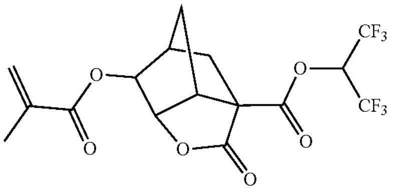

(m-22)

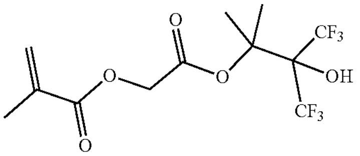

(m-23)

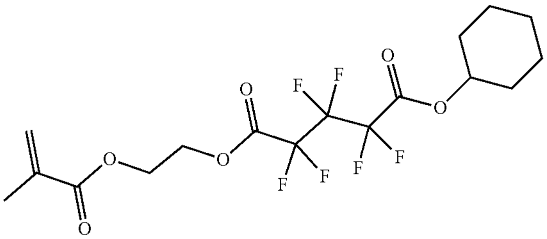

inside the reaction vessel was brought to 80° C., and the monomer solution was added dropwise over 3 hrs with stirring. The time of starting the dropwise addition was regarded as the time of starting the polymerization reaction, and the polymerization reaction was allowed to proceed for 6 hrs. After completion of the polymerization reaction, the polymerization solution was cooled to no greater than 30° C. by water cooling. The thus cooled polymerization solution was charged into methanol (2,000 parts by mass), and a thus precipitated white powder was filtered off. The white powder obtained by the filtration was washed twice with methanol and filtered off, followed by drying at 50° C. for 17 hrs to give a white powdery polymer (A-1) (yield: 80%). The Mw of the polymer (A-1) was 8,700, and the Mw/Mn was 1.49. Furthermore, as a result of the $^{13}$C-NMR analysis, the proportions of the structural units derived from (m-1), (m-2), and (m-10) were, respectively, 39.9 mol %, 14.3 mol %, and 45.8 mol %.

Synthesis Examples 26 to 32: Synthesis of Polymers (A-2) to (A-8

Polymers (A-2) to (A-8) were synthesized by a similar operation to that of Synthesis Example 25 except that each monomer of the type and in the proportion shown in Table 1 below was used. The proportion (mol %), the yield (%), and the physical property values (the Mw and the Mw/Mn) of each structural unit of each polymer thus obtained are shown together in Table 1 below. It is to be noted that in Table 1 below, "-" indicates that the corresponding monomer was not used.

TABLE 1

| | | Monomer that gives structural unit (I) | | | Monomer that gives structural unit (II) | | | Monomer that gives structural unit (III) | | | | |
|---|---|---|---|---|---|---|---|---|---|---|---|---|
| | (A) Polymer | type | usage proportion (mol %) | proportion of structural unit (mol %) | type | usage proportion (mol %) | proportion of structural unit (mol %) | type | usage proportion (mol %) | proportion of structural unit (mol %) | Mw | Mw/Mn |
| Synthesis Example 25 | A-1 | m-1<br>m-2 | 40<br>15 | 39.9<br>14.3 | m-10 | 45 | 45.8 | — | — | — | 8,700 | 1.49 |
| Synthesis Example 26 | A-2 | m-1<br>m-2 | 30<br>10 | 31.4<br>8.0 | m-11 | 60 | 60.6 | — | — | — | 9,000 | 1.44 |
| Synthesis Example 27 | A-3 | m-1<br>m-3 | 35<br>20 | 32.3<br>18.1 | m-13 | 45 | 49.6 | — | — | — | 8,500 | 1.59 |
| Synthesis Example 28 | A-4 | m-1<br>m-4 | 40<br>15 | 41.1<br>13.2 | m-9 | 45 | 45.7 | — | — | — | 8,700 | 1.44 |
| Synthesis Example 29 | A-5 | m-1<br>m-4 | 40<br>15 | 41.6<br>12.3 | m-8 | 45 | 46.1 | — | — | — | 7,700 | 1.51 |
| Synthesis Example 30 | A-6 | m-1 | 40 | 42.4 | m-7 | 45 | 39.5 | m-12 | 15 | 18.1 | 7,800 | 1.59 |
| Synthesis Example 31 | A-7 | m-1 | 50 | 51.0 | m-5 | 50 | 49.0 | — | — | — | 7,800 | 1.55 |
| Synthesis Example 32 | A-8 | m-1 | 40 | 42.8 | m-6 | 60 | 57.2 | — | — | — | 8,000 | 1.43 |

Synthesis Example 25: Synthesis of Polymer (A-1

The monomer (m-1), the monomer (m-2), and the monomer (m-10) were dissolved in 2-butanone (200 parts by mass) such that the molar ratio became 40/15/45 (mol %), and a monomer solution was prepared by adding AIBN (azobisisobutyronitrile) (2 mol % with respect to 100 mol % total of the monomers used) as an initiator. Into an empty reaction vessel was charged 2-butanone (100 parts by mass), and after purging with nitrogen for 30 min, a temperature

Synthesis Example 33: Synthesis of Polymer (A-9

The monomer (m-1) and the monomer (m-15) were dissolved in 1-methoxy-2-propanol (200 parts by mass) such that the molar ratio became 50/50 (mol %), and a monomer solution was prepared by adding AIBN (3 mol %) as an initiator. Into an empty reaction vessel was charged 1-methoxy-2-propanol (100 parts by mass), and after purging with nitrogen for 30 min, a temperature inside the reaction vessel was brought to 80° C., and the monomer solution was added dropwise over 3 hrs with stirring. The time of starting the dropwise addition was regarded as the time of starting the polymerization reaction, and the polymerization reaction was allowed to proceed for 6 hrs. After completion of the polymerization reaction, the polymerization solution was cooled to no greater than 30° C. by water cooling. The thus cooled polymerization solution was charged into hexane (2,000 parts by mass), and a thus precipitated white powder was filtered off. The white powder obtained by the filtration was washed twice with hexane and filtered off, and dissolved in 1-methoxy-2-propanol (300 parts by mass). Next, methanol (500 parts by mass), triethylamine (50 parts by mass), and ultra-pure water (10 parts by mass) were added thereto, and a hydrolysis reaction was performed at 70° C. for 6 hrs with stirring. After completion of the reaction, the remaining solvent was distilled away. A solid thus obtained was dissolved in acetone (100 parts by mass), followed by adding dropwise to water (500 parts by mass) to permit coagulation of the polymer. A solid thus obtained was filtered off, and drying at 50° C. for 13 hrs gave a white powdery polymer (A-9) (yield: 78%). The Mw of the polymer (A-9) was 7,700, and the Mw/Mn was 1.77. Furthermore, as a result of the $^{13}$C-NMR analysis, the proportions of the structural units derived from (m-1) and (m-15) were, respectively, 50.3 mol % and 49.7 mol %.

Synthesis Examples 34 to 35: Synthesis of Polymers (A-10) to (A-11

Polymers (A-10) to (A-11) were synthesized by a similar operation to that of Synthesis Example 33 except that each monomer of the type and in the proportion shown in Table 2 below was used. The proportion (mol %), the yield (%), and the physical property values (the Mw and the Mw/Mn) of each structural unit of each polymer thus obtained are shown together in Table 2 below.

TABLE 2

| | | Monomer that gives structural unit (I) | | | Monomer that gives structural unit (III) | | | Monomer that gives structural unit (IV) | | | | |
|---|---|---|---|---|---|---|---|---|---|---|---|---|
| | (A) Polymer | type | usage proportion (mol %) | proportion of structural unit (mol %) | type | usage proportion (mol %) | proportion of structural unit (mol %) | type | usage proportion (mol %) | proportion of structural unit (mol %) | Mw | Mw/Mn |
| Synthesis Example 33 | A-9 | m-1 | 50 | 50.3 | — | — | — | m-15 | 50 | 49.7 | 7,700 | 1.77 |
| Synthesis Example 34 | A-10 | m-1 | 50 | 50.7 | — | — | — | m-16 | 50 | 49.3 | 7,100 | 1.67 |
| Synthesis Example 35 | A-11 | m-1 | 40 | 41.2 | m-14 | 30 | 31.2 | m-15 | 30 | 27.6 | 7,000 | 1.59 |

Synthesis Example 36: Synthesis of Polymer (E-1

The monomer (F-1) and the monomer (m-2) were dissolved in 2-butanone (200 parts by mass) such that the molar ratio became 80/20 (mol %), and a monomer solution was prepared by adding AIBN (3 mol %) as an initiator. Into an empty reaction vessel was charged 2-butanone (100 parts by mass), and after purging with nitrogen for 30 min, a temperature inside the reaction vessel was brought to 80° C., and the monomer solution was added dropwise over 3 hrs with stirring. The time of starting the dropwise addition was regarded as the time of starting the polymerization reaction, and the polymerization reaction was allowed to proceed for 6 hrs. After completion of the polymerization reaction, the polymerization solution was cooled to no greater than 30° C. by water cooling. The solvent was replaced with acetonitrile (400 parts by mass), and then an operation of adding hexane (100 parts by mass) and stirring to collect an acetonitrile layer was repeated three times. The solvent was replaced with propylene glycol monomethyl ether acetate to give a solution of the polymer (E-1) (yield: 77%). The Mw of the polymer (E-1) was 7,100, and the Mw/Mn was 1.51. Furthermore, as a result of the $^{13}$C-NMR analysis, the proportions of the structural units derived from (F-1) and (m-2) were, respectively, 81.2 mol % and 18.8 mol %.

Synthesis Examples 37 to 62: Synthesis of Polymers (E-2) to (E-27

Polymers (E-2) to (E-27) were synthesized by a similar operation to that of Synthesis Example 36 except that each monomer of the type and in the proportion shown in Table 3 below was used. The proportion (mol %), the yield (%), and the physical property values (the Mw and the Mw/Mn) of each structural unit of each polymer thus obtained are shown together in Table 3 below.

TABLE 3

| | | Monomer that gives structural unit (T) | | | Monomer that gives structural unit (I) | | | Monomer that gives structural unit (III) | | | Monomer that gives structural unit (F) | | | | |
|---|---|---|---|---|---|---|---|---|---|---|---|---|---|---|---|
| | (E) Polymer | type | usage proportion (mol %) | proportion of structural unit (mol %) | type | usage proportion (mol %) | proportion of structural unit (mol %) | type | usage proportion (mol %) | proportion of structural unit (mol %) | type | usage proportion (mol %) | proportion of structural unit (mol %) | Mw | Mw/Mn |
| Synthesis Example 36 | E-1 | F-1 | 80 | 81.2 | m-2 | 20 | 18.8 | — | — | — | — | — | — | 7,100 | 1.51 |
| Synthesis Example 37 | E-2 | F-2 | 80 | 80.9 | m-20 | 20 | 19.1 | — | — | — | — | — | — | 6,900 | 1.62 |
| Synthesis Example 38 | E-3 | F-3 | 100 | 100 | — | — | — | — | — | — | — | — | — | 8,500 | 1.66 |
| Synthesis Example 39 | E-4 | F-1 | 80 | 79.1 | — | — | — | m-14 | 20 | 20.9 | — | — | — | 7,700 | 1.60 |
| Synthesis Example 40 | E-5 | F-2 | 90 | 89.4 | — | — | — | — | — | — | m-17 | 10 | 10.6 | 7,000 | 1.52 |
| Synthesis Example 41 | E-6 | F-3 | 60 | 59.4 | m-1 | 20 | 21.2 | — | — | — | m-18 | 20 | 19.4 | 7,200 | 1.62 |
| Synthesis Example 42 | E-7 | F-4 | 80 | 81.1 | m-1 | 20 | 18.9 | — | — | — | — | — | — | 6,800 | 1.58 |
| Synthesis Example 43 | E-8 | F-5 | 90 | 90.6 | m-20 | 10 | 9.4 | — | — | — | — | — | — | 7,500 | 1.66 |
| Synthesis Example 44 | E-9 | F-6 | 70 | 70.6 | m-3 | 15 | 14.6 | — | — | — | m-17 | 15 | 14.8 | 7,100 | 1.57 |
| Synthesis Example 45 | E-10 | F-7 | 80 | 81.2 | m-20 | 10 | 9.8 | m-14 | 10 | 9.0 | — | — | — | 7,200 | 1.55 |
| Synthesis Example 46 | E-11 | F-8 | 70 | 69.9 | m-2 | 30 | 30.1 | — | — | — | — | — | — | 6,600 | 1.54 |
| Synthesis Example 47 | E-12 | F-9 | 70 | 69.5 | m-4 | 15 | 14.3 | m-14 | 15 | 16.2 | — | — | — | 8,000 | 1.61 |
| Synthesis Example 48 | E-13 | F-10 | 50 | 51.8 | m-3 | 25 | 23.9 | — | — | — | m-18 | 25 | 24.3 | 7,400 | 1.69 |
| Synthesis Example 49 | E-14 | F-11 | 70 | 70.1 | m-2 | 15 | 13.8 | — | — | — | m-19 | 15 | 16.1 | 8,100 | 1.55 |
| Synthesis Example 50 | E-15 | F-12 | 70 | 70.9 | m-20 | 15 | 14.2 | m-14 | 15 | 14.9 | — | — | — | 6,900 | 1.61 |
| Synthesis Example 51 | E-16 | F-13 | 50 | 51.2 | m-4 | 30 | 29.8 | — | — | — | m-17 | 20 | 19.0 | 7,100 | 1.57 |
| Synthesis Example 52 | E-17 | F-14 | 70 | 70.3 | m-20 | 10 | 9.1 | m-14 | 10 | 10.7 | m-17 | 10 | 9.9 | 8,200 | 1.51 |
| Synthesis Example 53 | E-18 | F-15 | 10 | 10.9 | m-20 | 30 | 30.7 | — | — | — | m-18 | 60 | 58.4 | 7,900 | 1.61 |
| Synthesis Example 54 | E-19 | F-16 | 10 | 9.8 | m-2 | 30 | 30.1 | — | — | — | m-18 | 60 | 60.1 | 7,700 | 1.66 |
| Synthesis Example 55 | E-20 | F-17 | 70 | 71.0 | m-4 | 10 | 9.1 | m-14 | 10 | 9.2 | m-19 | 10 | 10.7 | 7,100 | 1.52 |
| Synthesis Example 56 | E-21 | F-18 | 80 | 79.6 | m-20 | 10 | 9.9 | — | — | — | m-17 | 10 | 10.5 | 6,800 | 1.59 |
| Synthesis Example 57 | E-22 | F-19 | 80 | 81.4 | m-4 | 20 | 18.6 | — | — | — | — | — | — | 8,100 | 1.54 |
| Synthesis Example 58 | E-23 | F-20 | 80 | 81.9 | m-20 | 10 | 8.9 | — | — | — | m-18 | 10 | 9.2 | 8,000 | 1.61 |
| Synthesis Example 59 | E-24 | F-21 | 50 | 50.8 | m-1 | 20 | 19.4 | m-14 | 30 | 29.8 | — | — | — | 7,400 | 1.54 |
| Synthesis Example 60 | E-25 | F-22 | 20 | 20.4 | m-2 | 40 | 40.8 | — | — | — | m-18 | 40 | 38.8 | 7,000 | 1.53 |
| Synthesis Example 61 | E-26 | F-23 | 50 | 50.5 | m-20 | 10 | 9.9 | — | — | — | m-19 | 40 | 39.6 | 7,300 | 1.67 |
| Synthesis Example 62 | E-27 | F-24 | 70 | 70.9 | m-4 | 10 | 8.9 | m-14 | 10 | 10.5 | m-17 | 10 | 9.7 | 8,100 | 1.59 |

Synthesis Examples 63 to 73: Synthesis of Polymers (E-28) to (E-38

Polymers (E-28) to (E-38) were synthesized by a similar operation to that of Synthesis Example 36 except that each monomer of the type and in the proportion shown in Table 4 below was used. The proportion (mol %), the yield (%), and the physical property values (the Mw and the Mw/Mn) of each structural unit of each polymer thus obtained are shown together in Table 4 below.

TABLE 4

| | | Monomer that gives structural unit (F) | | | Monomer that gives structural unit (I) | | | Monomer that gives structural unit (III) | | | | |
|---|---|---|---|---|---|---|---|---|---|---|---|---|
| | (E) Polymer | type | usage proportion (mol %) | proportion of structural unit (mol %) | type | usage proportion (mol %) | proportion of structural unit (mol %) | type | usage proportion (mol %) | proportion of structural unit (mol %) | Mw | Mw/ Mn |
| Synthesis Example 63 | E-28 | m-18 | 80 | 81.3 | m-2 | 20 | 18.7 | — | — | — | 7,700 | 1.66 |
| Synthesis Example 64 | E-29 | m-18 | 80 | 82.1 | m-20 | 20 | 17.9 | — | — | — | 6,700 | 1.62 |
| Synthesis Example 65 | E-30 | m-18 | 100 | 100.0 | — | — | — | — | — | — | 7,800 | 1.59 |
| Synthesis Example 66 | E-31 | m-18 | 80 | 78.9 | — | — | — | m-14 | 20 | 21.1 | 8,100 | 1.77 |
| | | | | | — | — | — | | | | | |
| Synthesis Example 67 | E-32 | m-18 | 90 | 91.2 | — | — | — | — | — | — | 7,800 | 1.65 |
| | | m-17 | 10 | 8.8 | | | | | | | | |
| Synthesis Example 68 | E-33 | m-19 | 90 | 89.9 | m-20 | 10 | 10.1 | — | — | — | 8,000 | 1.55 |
| Synthesis Example 69 | E-34 | m-19 | 70 | 67.3 | m-3 | 15 | 16.4 | — | — | — | 7,700 | 1.69 |
| | | m-17 | 15 | 16.3 | | | | | | | | |
| Synthesis Example 70 | E-35 | m-21 | 70 | 70.9 | m-4 | 15 | 14.5 | m-14 | 15 | 14.6 | 7,100 | 1.59 |
| Synthesis Example 71 | E-36 | m-22 | 50 | 51.1 | m-4 | 30 | 28.4 | — | — | — | 7,500 | 1.61 |
| | | m-17 | 20 | 20.5 | | | | | | | | |
| Synthesis Example 72 | E-37 | m-23 | 70 | 68.7 | m-20 | 10 | 10.4 | m-14 | 10 | 10.6 | 8,000 | 1.62 |
| | | m-17 | 10 | 10.3 | | | | | | | | |
| Synthesis Example 73 | E-38 | m-23 | 70 | 70.3 | m-20 | 15 | 15.3 | m-14 | 15 | 14.4 | 6,900 | 1.58 |

Preparation of Radiation-Sensitive Resin Composition

Components other than the polymer (A) and the polymer (E) used in preparing each radiation-sensitive resin composition are shown below.

(B) Acid Generating Agent

B-1 to B-6: Compounds represented by the following formulae (B-1) to (B-6)

(B-1)

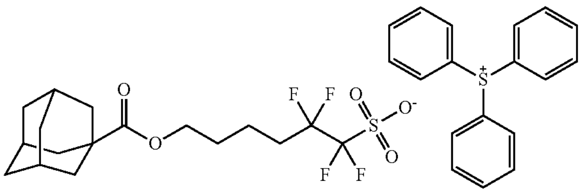

(B-2)

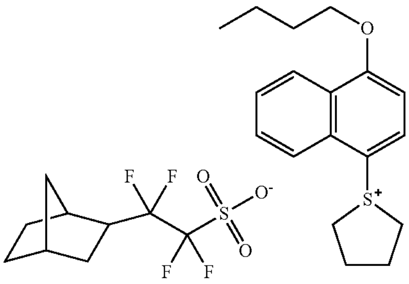

-continued (B-3)

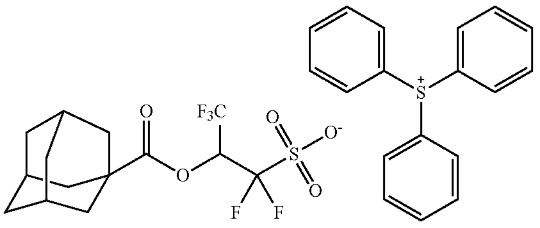

(B-4)

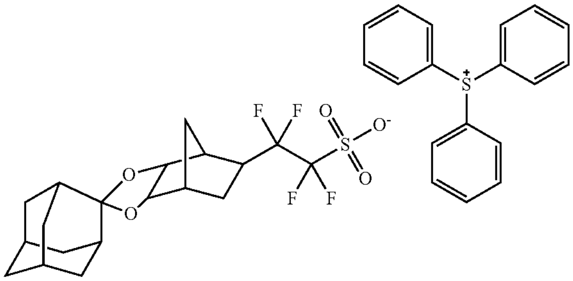

(B-5)

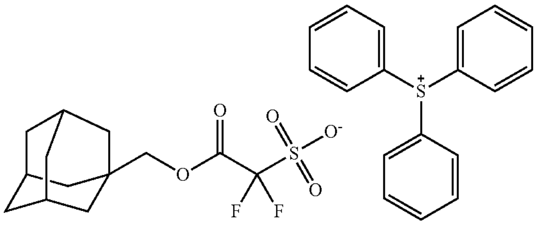

(B-6)

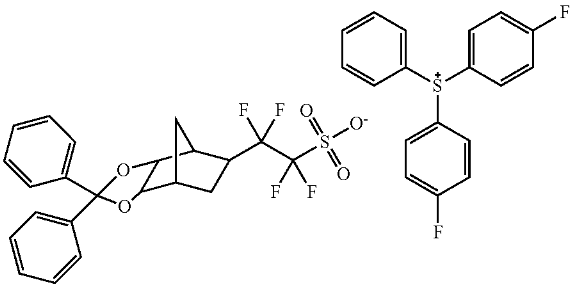

(C) Acid Diffusion Control Agent

C-1 to C-5: Compounds represented by the following formulae (C-1) to (C-5)

(C-1)

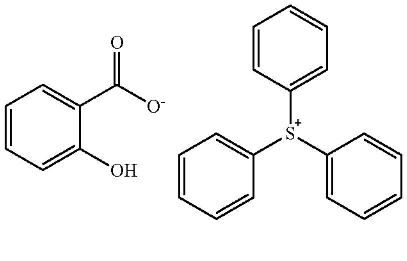

-continued (C-2)

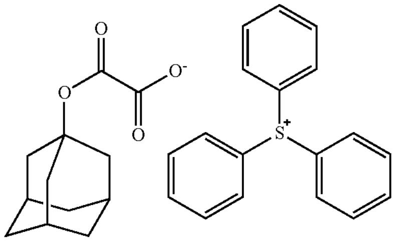

(C-3)

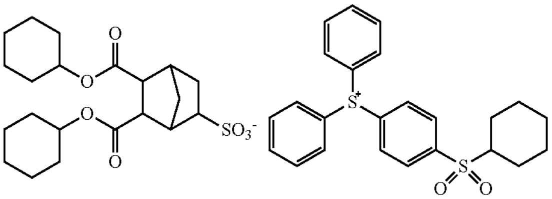

(C-4)

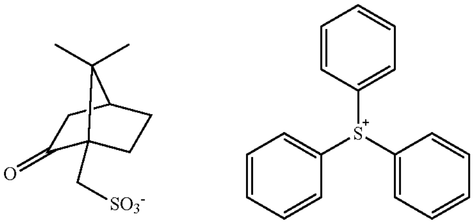

(C-5)

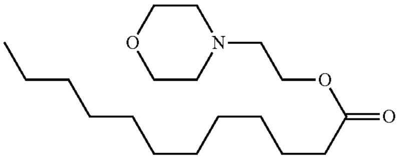

(D) Solvent

D-1: propylene glycol monomethyl ether acetate

D-2: cyclohexanone

D-3: γ-butyrolactone

D-4: ethyl lactate

Preparation of Positive-Tone Radiation-Sensitive Resin Composition for ArF Exposure

Example 1

A radiation-sensitive resin composition (J-1) was prepared by: mixing 100 parts by mass of (A-1) as the polymer (A), 14.0 parts by mass of (B-4) as the acid generating agent (B), 2.3 parts by mass of (C-1) as the acid diffusion control agent (C), 3.0 parts by mass (solid content) of (E-1) as the polymer (E), and 3,230 parts by mass of a mixed solvent of (D-1)/(D-2)/(D-3) as the solvent (D); and filtering a resulting mixture through a membrane filter having a pore size of 0.2 μm.

Examples 2 to 51 and Comparative Examples 1 to 11

Radiation-sensitive resin compositions (J-2) to (J-51) and (CJ-1) to (CJ-11) were prepared in a similar manner to Example 1, except that for each component, the type and content shown in Table 5 below were used.

TABLE 5

| | Radiation-sensitive resin composition | (A) Polymer type | (A) Polymer content (parts by mass) | (B) Acid generating agent type | (B) Acid generating agent content (parts by mass) | (C) Acid diffusion control agent type | (C) Acid diffusion control agent content (parts by mass) | (E) Polymer type | (E) Polymer content (parts by mass) | (D) solvent type | (D) solvent content (parts by mass) |
|---|---|---|---|---|---|---|---|---|---|---|---|
| Example 1 | J-1 | A-1 | 100 | B-4 | 14.0 | C-1 | 2.3 | E-1 | 3.0 | D-1/D-2/D-3 | 2,240/960/30 |
| Example 2 | J-2 | A-1 | 100 | B-4 | 14.0 | C-1 | 2.3 | E-2 | 3.0 | D-1/D-2/D-3 | 2,240/960/30 |
| Example 3 | J-3 | A-1 | 100 | B-4 | 14.0 | C-1 | 2.3 | E-3 | 3.0 | D-1/D-2/D-3 | 2,240/960/30 |
| Example 4 | J-4 | A-1 | 100 | B-4 | 14.0 | C-1 | 2.3 | E-4 | 3.0 | D-1/D-2/D-3 | 2,240/960/30 |
| Example 5 | J-5 | A-1 | 100 | B-4 | 14.0 | C-1 | 2.3 | E-5 | 3.0 | D-1/D-2/D-3 | 2,240/960/30 |
| Example 6 | J-6 | A-1 | 100 | B-4 | 14.0 | C-1 | 2.3 | E-6 | 3.0 | D-1/D-2/D-3 | 2,240/960/30 |
| Example 7 | J-7 | A-1 | 100 | B-4 | 14.0 | C-1 | 2.3 | E-7 | 3.0 | D-1/D-2/D-3 | 2,240/960/30 |
| Example 8 | J-8 | A-1 | 100 | B-4 | 14.0 | C-1 | 2.3 | E-8 | 3.0 | D-1/D-2/D-3 | 2,240/960/30 |
| Example 9 | J-9 | A-1 | 100 | B-4 | 14.0 | C-1 | 2.3 | E-9 | 3.0 | D-1/D-2/D-3 | 2,240/960/30 |
| Example 10 | J-10 | A-1 | 100 | B-4 | 14.0 | C-1 | 2.3 | E-10 | 3.0 | D-1/D-2/D-3 | 2,240/960/30 |
| Example 11 | J-11 | A-1 | 100 | B-4 | 14.0 | C-1 | 2.3 | E-11 | 3.0 | D-1/D-2/D-3 | 2,240/960/30 |
| Example 12 | J-12 | A-1 | 100 | B-4 | 14.0 | C-1 | 2.3 | E-12 | 3.0 | D-1/D-2/D-3 | 2,240/960/30 |
| Example 13 | J-13 | A-1 | 100 | B-4 | 14.0 | C-1 | 2.3 | E-13 | 3.0 | D-1/D-2/D-3 | 2,240/960/30 |
| Example 14 | J-14 | A-1 | 100 | B-4 | 14.0 | C-1 | 2.3 | E-14 | 3.0 | D-1/D-2/D-3 | 2,240/960/30 |
| Example 15 | J-15 | A-1 | 100 | B-4 | 14.0 | C-1 | 2.3 | E-15 | 3.0 | D-1/D-2/D-3 | 2,240/960/30 |
| Example 16 | J-16 | A-1 | 100 | B-4 | 14.0 | C-1 | 2.3 | E-16 | 3.0 | D-1/D-2/D-3 | 2,240/960/30 |
| Example 17 | J-17 | A-1 | 100 | B-4 | 14.0 | C-1 | 2.3 | E-17 | 3.0 | D-1/D-2/D-3 | 2,240/960/30 |
| Example 18 | J-18 | A-1 | 100 | B-4 | 14.0 | C-1 | 2.3 | E-18 | 3.0 | D-1/D-2/D-3 | 2,240/960/30 |
| Example 19 | J-19 | A-1 | 100 | B-4 | 14.0 | C-1 | 2.3 | E-19 | 3.0 | D-1/D-2/D-3 | 2,240/960/30 |
| Example 20 | J-20 | A-1 | 100 | B-4 | 14.0 | C-1 | 2.3 | E-20 | 3.0 | D-1/D-2/D-3 | 2,240/960/30 |
| Example 21 | J-21 | A-1 | 100 | B-4 | 14.0 | C-1 | 2.3 | E-21 | 3.0 | D-1/D-2/D-3 | 2,240/960/30 |
| Example 22 | J-22 | A-1 | 100 | B-4 | 14.0 | C-1 | 2.3 | E-22 | 3.0 | D-1/D-2/D-3 | 2,240/960/30 |
| Example 23 | J-23 | A-1 | 100 | B-4 | 14.0 | C-1 | 2.3 | E-23 | 3.0 | D-1/D-2/D-3 | 2,240/960/30 |
| Example 24 | J-24 | A-1 | 100 | B-4 | 14.0 | C-1 | 2.3 | E-24 | 3.0 | D-1/D-2/D-3 | 2,240/960/30 |
| Example 25 | J-25 | A-1 | 100 | B-4 | 14.0 | C-1 | 2.3 | E-25 | 3.0 | D-1/D-2/D-3 | 2,240/960/30 |
| Example 26 | J-26 | A-1 | 100 | B-4 | 14.0 | C-1 | 2.3 | E-26 | 3.0 | D-1/D-2/D-3 | 2,240/960/30 |
| Example 27 | J-27 | A-1 | 100 | B-4 | 14.0 | C-1 | 2.3 | E-27 | 3.0 | D-1/D-2/D-3 | 2,240/960/30 |
| Example 28 | J-28 | A-2 | 100 | B-4 | 14.0 | C-1 | 2.3 | E-1 | 3.0 | D-1/D-2/D-3 | 2,240/960/30 |
| Example 29 | J-29 | A-3 | 100 | B-4 | 14.0 | C-1 | 2.3 | E-1 | 3.0 | D-1/D-2/D-3 | 2,240/960/30 |
| Example 30 | J-30 | A-4 | 100 | B-4 | 14.0 | C-1 | 2.3 | E-1 | 3.0 | D-1/D-2/D-3 | 2,240/960/30 |
| Example 31 | J-31 | A-5 | 100 | B-4 | 14.0 | C-1 | 2.3 | E-1 | 3.0 | D-1/D-2/D-3 | 2,240/960/30 |
| Example 32 | J-32 | A-6 | 100 | B-4 | 14.0 | C-1 | 2.3 | E-1 | 3.0 | D-1/D-2/D-3 | 2,240/960/30 |
| Example 33 | J-33 | A-7 | 100 | B-4 | 14.0 | C-1 | 2.3 | E-1 | 3.0 | D-1/D-2/D-3 | 2,240/960/30 |
| Example 34 | J-34 | A-8 | 100 | B-4 | 14.0 | C-1 | 2.3 | E-1 | 3.0 | D-1/D-2/D-3 | 2,240/960/30 |
| Example 35 | J-35 | A-1 | 100 | B-1 | 14.0 | C-1 | 2.3 | E-1 | 3.0 | D-1/D-2/D-3 | 2,240/960/30 |
| Example 36 | J-36 | A-1 | 100 | B-2 | 14.0 | C-1 | 2.3 | E-1 | 3.0 | D-1/D-2/D-3 | 2,240/960/30 |
| Example 37 | J-37 | A-1 | 100 | B-3 | 14.0 | C-1 | 2.3 | E-1 | 3.0 | D-1/D-2/D-3 | 2,240/960/30 |
| Example 38 | J-38 | A-1 | 100 | B-5 | 14.0 | C-1 | 2.3 | E-1 | 3.0 | D-1/D-2/D-3 | 2,240/960/30 |
| Example 39 | J-39 | A-1 | 100 | B-6 | 14.0 | C-1 | 2.3 | E-1 | 3.0 | D-1/D-2/D-3 | 2,240/960/30 |
| Example 40 | J-40 | A-1 | 100 | B-4 | 14.0 | C-2 | 2.3 | E-1 | 3.0 | D-1/D-2/D-3 | 2,240/960/30 |
| Example 41 | J-41 | A-1 | 100 | B-4 | 14.0 | C-3 | 2.3 | E-1 | 3.0 | D-1/D-2/D-3 | 2,240/960/30 |
| Example 42 | J-42 | A-1 | 100 | B-4 | 14.0 | C-4 | 2.3 | E-1 | 3.0 | D-1/D-2/D-3 | 2,240/960/30 |
| Example 43 | J-43 | A-1 | 100 | B-4 | 14.0 | C-5 | 2.3 | E-1 | 3.0 | D-1/D-2/D-3 | 2,240/960/30 |
| Example 44 | J-44 | A-1 | 100 | B-4 | 14.0 | C-1 | 2.3 | E-1 | 0.3 | D-1/D-2/D-3 | 2,240/960/30 |
| Example 45 | J-45 | A-1 | 100 | B-4 | 14.0 | C-1 | 2.3 | E-1 | 1.5 | D-1/D-2/D-3 | 2,240/960/30 |
| Example 46 | J-46 | A-1 | 100 | B-4 | 14.0 | C-1 | 2.3 | E-1 | 6.0 | D-1/D-2/D-3 | 2,240/960/30 |
| Example 47 | J-47 | A-1 | 100 | B-4 | 14.0 | C-1 | 2.3 | E-1 | 10.0 | D-1/D-2/D-3 | 2,240/960/30 |
| Example 48 | J-48 | A-1 | 100 | B-4 | 14.0 | C-1 | 2.3 | E-1 | 25.0 | D-1/D-2/D-3 | 2,240/960/30 |
| Example 49 | J-49 | A-1 | 100 | B-4 | 14.0 | C-1 | 2.3 | E-1/E-27 | 0.01/1.0 | D-1/D-2/D-3 | 2,240/960/30 |
| Example 50 | J-50 | A-1 | 100 | B-4 | 14.0 | C-1 | 2.3 | E-1/E-27 | 1.0/1.0 | D-1/D-2/D-3 | 2,240/960/30 |
| Example 51 | J-51 | A-1 | 100 | B-4 | 14.0 | C-1 | 2.3 | E-1/E-27 | 10.0/1.0 | D-1/D-2/D-3 | 2,240/960/30 |
| Comparative Example 1 | CJ-1 | A-1 | 100 | B-4 | 14.0 | C-1 | 2.3 | E-28 | 3.0 | D-1/D-2/D-3 | 2,240/960/30 |
| Comparative Example 2 | CJ-2 | A-1 | 100 | B-4 | 14.0 | C-1 | 2.3 | E-29 | 3.0 | D-1/D-2/D-3 | 2,240/960/30 |
| Comparative Example 3 | CJ-3 | A-1 | 100 | B-4 | 14.0 | C-1 | 2.3 | E-30 | 3.0 | D-1/D-2/D-3 | 2,240/960/30 |
| Comparative Example 4 | CJ-4 | A-1 | 100 | B-4 | 14.0 | C-1 | 2.3 | E-31 | 3.0 | D-1/D-2/D-3 | 2,240/960/30 |
| Comparative Example 5 | CJ-5 | A-1 | 100 | B-4 | 14.0 | C-1 | 2.3 | E-32 | 3.0 | D-1/D-2/D-3 | 2,240/960/30 |
| Comparative Example 6 | CJ-6 | A-1 | 100 | B-4 | 14.0 | C-1 | 2.3 | E-33 | 3.0 | D-1/D-2/D-3 | 2,240/960/30 |
| Comparative Example 7 | CJ-7 | A-1 | 100 | B-4 | 14.0 | C-1 | 2.3 | E-34 | 3.0 | D-1/D-2/D-3 | 2,240/960/30 |
| Comparative Example 8 | CJ-8 | A-1 | 100 | B-4 | 14.0 | C-1 | 2.3 | E-35 | 3.0 | D-1/D-2/D-3 | 2,240/960/30 |
| Comparative Example 9 | CJ-9 | A-1 | 100 | B-4 | 14.0 | C-1 | 2.3 | E-36 | 3.0 | D-1/D-2/D-3 | 2,240/960/30 |
| Comparative Example 10 | CJ-10 | A-1 | 100 | B-4 | 14.0 | C-1 | 2.3 | E-37 | 3.0 | D-1/D-2/D-3 | 2,240/960/30 |

TABLE 5-continued

| | Radiation-sensitive resin composition | (A) Polymer type | (A) Polymer content (parts by mass) | (B) Acid generating agent type | (B) Acid generating agent content (parts by mass) | (C) Acid diffusion control agent type | (C) Acid diffusion control agent content (parts by mass) | (E) Polymer type | (E) Polymer content (parts by mass) | (D) solvent type | (D) solvent content (parts by mass) |
|---|---|---|---|---|---|---|---|---|---|---|---|
| Comparative Example 11 | CJ-11 | A-1 | 100 | B-4 | 14.0 | C-1 | 2.3 | E-38 | 3.0 | D-1/D-2/D-3 | 2,240/960/30 |

Formation of Resist Pattern Using Positive-Tone Radiation-Sensitive Resin Composition for ArF Exposure An underlayer antireflective film having an average thickness of 105 nm was formed by applying a composition for underlayer antireflective film formation ("ARC66," available from Brewer Science, Inc.) on a 12-inch silicon wafer using a spin-coater ("CLEAN TRACK ACT 12," available from Tokyo Electron Limited), and thereafter heating the composition at 205° C. for 60 sec. Each positive-tone radiation-sensitive resin composition for ArF exposure prepared as described above was applied on the underlayer antireflective film using the spin-coater, and subjected to PB (prebaking) at 90° C. for 60 sec. Thereafter, by cooling at 23° C. for 30 sec, a resist film having an average thickness of 90 nm was formed. Next, the resist pattern was exposed using an ArF excimer laser immersion exposure system ("TWINSCAN XT-1900i," available from ASML Co.) through a mask pattern having spaces of 40 nm and pitches of 105 nm at optical conditions involving: NA of 1.35, and Annular (σ=0.8/0.6). After the exposure, PEB (post-exposure baking) was carried out at 90° C. for 60 sec. Thereafter, the resist film was subjected to development with an alkali using a 2.38% by mass aqueous TMAH solution as an alkaline developer solution. After the development, washing with water was carried out, followed by further drying, to form a positive-tone resist pattern (40 nm line-and-space pattern).

Evaluations

The resist patterns formed using the radiation-sensitive resin compositions for ArF exposure were evaluated on the sensitivity and the number of post-development defects in accordance with the below methods. Furthermore, the resist films before the ArF exposure were evaluated on the receding contact angle in accordance with the below method. The results are shown in Table 6 below. It is to be noted that line width measurement of the resist patterns was performed using a scanning electron microscope ("CG-5000," available from Hitachi High-Technologies Corporation).

Sensitivity

An exposure dose at which a 40 nm line-and-space pattern was formed in the aforementioned resist pattern formation using the radiation-sensitive resin composition for ArF exposure was defined as an optimum exposure dose, and this optimum exposure dose was adopted as sensitivity (mJ/$cm^2$). The sensitivity was evaluated to be: "favorable" in a case of being no greater than 26 mJ/$cm^2$; and "unfavorable" in a case of being greater than 26 mJ/$cm^2$.

Post-PB Receding Contact Angle

With regard to the resist film before the ArF exposure in the method of forming a resist pattern, the receding contact angle was measured by the following procedure using DSA-10, available from KRUSS Scientific, in an environment having a room temperature of 23° C., a relative humidity of 40%, and normal pressure.

Water was discharged from the needle of the DSA-10 to form a 25 μl water droplet on the resist film. The water droplet was aspirated through the needle for 90 sec at a rate of 10 μl/min, and the contact angle was measured every second (90 times in total). In the measurement, the average value of 20 contact angles after the contact angle became stable was calculated, and taken as the post-PB receding contact angle)(°. The post-PB receding contact angle was evaluated to be: "favorable" in a case of being no less than 70°; and "unfavorable" in a case of being less than 70°.

Number of Development Defects

The resist film was exposed at the optimum radiation dose to form a line-and-space pattern having a line width of 40 nm, and used as a wafer for defect inspection. The number of defects on the wafer for defect inspection was measured using a defect inspection device ("KLA2810," available from KLA-Tencor). The number of post-development defects was evaluated to be: "favorable" in a case of the number of defects judged to be derived from the resist film being no greater than 15; and "unfavorable" in a case of the number of such defects being greater than 15.

TABLE 6

| | Radiation-sensitive resin composition | Sensitivity (mJ/$cm^2$) | Receding contact angle/ post-PB (°) | Number of development defects |
|---|---|---|---|---|
| Example 1 | J-1 | 24.7 | 81 | 0 |
| Example 2 | J-2 | 24.5 | 78 | 1 |
| Example 3 | J-3 | 24.3 | 85 | 7 |
| Example 4 | J-4 | 24.7 | 81 | 0 |
| Example 5 | J-5 | 24.8 | 82 | 1 |
| Example 6 | J-6 | 25.1 | 81 | 8 |
| Example 7 | J-7 | 24.1 | 86 | 2 |
| Example 8 | J-8 | 24.6 | 77 | 3 |
| Example 9 | J-9 | 24.1 | 79 | 9 |
| Example 10 | J-10 | 24.3 | 78 | 1 |
| Example 11 | J-11 | 24.8 | 81 | 0 |
| Example 12 | J-12 | 24.1 | 84 | 0 |
| Example 13 | J-13 | 23.9 | 78 | 2 |
| Example 14 | J-14 | 24.7 | 85 | 3 |
| Example 15 | J-15 | 25.3 | 81 | 1 |
| Example 16 | J-16 | 24.9 | 78 | 9 |
| Example 17 | J-17 | 23.5 | 85 | 5 |
| Example 18 | J-18 | 24.8 | 81 | 0 |
| Example 19 | J-19 | 24.8 | 78 | 7 |
| Example 20 | J-20 | 24.3 | 77 | 1 |
| Example 21 | J-21 | 24.6 | 79 | 2 |
| Example 22 | J-22 | 24.1 | 77 | 5 |
| Example 23 | J-23 | 25.3 | 76 | 0 |
| Example 24 | J-24 | 23.8 | 81 | 1 |
| Example 25 | J-25 | 24.5 | 84 | 7 |
| Example 26 | J-26 | 24.5 | 82 | 2 |
| Example 27 | J-27 | 24.1 | 81 | 2 |
| Example 28 | J-28 | 24.2 | 80 | 6 |
| Example 29 | J-29 | 24.3 | 81 | 9 |
| Example 30 | J-30 | 24.8 | 79 | 1 |
| Example 31 | J-31 | 24.6 | 80 | 5 |
| Example 32 | J-32 | 24.4 | 79 | 2 |
| Example 33 | J-33 | 24.3 | 85 | 7 |

TABLE 6-continued

| | Radiation-sensitive resin composition | Sensitivity (mJ/cm$^2$) | Receding contact angle/ post-PB (°) | Number of development defects |
|---|---|---|---|---|
| Example 34 | J-34 | 24.7 | 81 | 2 |
| Example 35 | J-35 | 22.8 | 81 | 1 |
| Example 36 | J-36 | 23.2 | 81 | 5 |
| Example 37 | J-37 | 24.7 | 80 | 3 |
| Example 38 | J-38 | 24.8 | 82 | 3 |
| Example 39 | J-39 | 24.2 | 81 | 5 |
| Example 40 | J-40 | 24.1 | 81 | 2 |
| Example 41 | J-41 | 21.2 | 81 | 8 |
| Example 42 | J-42 | 22.9 | 80 | 2 |
| Example 43 | J-43 | 22.6 | 82 | 2 |
| Example 44 | J-44 | 24.3 | 78 | 9 |
| Example 45 | J-45 | 24.7 | 79 | 0 |
| Example 46 | J-46 | 24.8 | 81 | 0 |
| Example 47 | J-47 | 24.8 | 82 | 7 |
| Example 48 | J-48 | 25.2 | 80 | 7 |
| Example 49 | J-49 | 25.5 | 76 | 13 |
| Example 50 | J-50 | 24.8 | 80 | 6 |
| Example 51 | J-51 | 24.6 | 82 | 4 |
| Comparative Example 1 | CJ-1 | 27.9 | 62 | 128 |
| Comparative Example 2 | CJ-2 | 27.2 | 67 | 171 |
| Comparative Example 3 | CJ-3 | 28.9 | 61 | 257 |
| Comparative Example 4 | CJ-4 | 27.1 | 64 | 320 |
| Comparative Example 5 | CJ-5 | 29.9 | 65 | 355 |
| Comparative Example 6 | CJ-6 | 27.1 | 66 | 64 |
| Comparative Example 7 | CJ-7 | 27.6 | 61 | 77 |
| Comparative Example 8 | CJ-8 | 28.8 | 67 | 231 |
| Comparative Example 9 | CJ-9 | 28.4 | 66 | 189 |
| Comparative Example 10 | CJ-10 | 27.9 | 69 | 174 |

TABLE 6-continued

| | Radiation-sensitive resin composition | Sensitivity (mJ/cm$^2$) | Receding contact angle/ post-PB (°) | Number of development defects |
|---|---|---|---|---|
| Comparative Example 11 | CJ-11 | 29.1 | 68 | 98 |

From the results in Table 6, it is revealed that when the radiation-sensitive resin compositions of the Examples were used for ArF exposure, the sensitivity, the post-PB receding contact angle performance, and the post-development defect performance were favorable. In contrast, in the case of the Comparative Examples, each characteristic was inferior compared to the Examples. Thus, in the case of using the radiation-sensitive resin compositions of the Examples for ArF exposure, a resist pattern can be formed with high sensitivity, and having superior water repellency and few defects.

Preparation of Radiation-Sensitive Resin Composition for Exposure to Extreme Ultraviolet Ray (EUV)

Example 52

A radiation-sensitive resin composition (J-52) was prepared by: mixing 100 parts by mass of (A-9) as the polymer (A), 14.0 parts by mass of (B-4) as the acid generating agent (B), 2.3 parts by mass of (C-1) as the acid diffusion control agent (C), 3.0 parts by mass of (E-1) as the polymer (E), and 6,110 parts by mass of a mixed solvent of (D-1)/(D-4) as the solvent (D); and filtering a resulting mixture through a membrane filter having a pore size of 0.2 μm.

Examples 53 to 79 and Comparative Examples 12 to 18

Radiation-sensitive resin compositions (J-53) to (J-79) and (CJ-12) to (CJ-18) were prepared in a similar manner to Example 52, except that for each component, the type and content shown in Table 7 below were used.

TABLE 7

| | Radiation-sensitive resin composition | (A) Polymer type | (A) Polymer content (parts by mass) | (B) Acid generating agent type | (B) Acid generating agent content (parts by mass) | (C) Acid diffusion control agent type | (C) Acid diffusion control agent content (parts by mass) | (E) Polymer type | (E) Polymer content (parts by mass) | (D) solvent type | (D) solvent content (parts by mass) |
|---|---|---|---|---|---|---|---|---|---|---|---|
| Example 52 | J-52 | A-9 | 100 | B-4 | 14.0 | C-1 | 2.3 | E-1 | 3.0 | D-1/D-4 | 4,280/1,830 |
| Example 53 | J-53 | A-9 | 100 | B-4 | 14.0 | C-1 | 2.3 | E-4 | 3.0 | D-1/D-4 | 4,280/1,830 |
| Example 54 | J-54 | A-9 | 100 | B-4 | 14.0 | C-1 | 2.3 | E-5 | 3.0 | D-1/D-4 | 4,280/1,830 |
| Example 55 | J-55 | A-9 | 100 | B-4 | 14.0 | C-1 | 2.3 | E-8 | 3.0 | D-1/D-4 | 4,280/1,830 |
| Example 56 | J-56 | A-9 | 100 | B-4 | 14.0 | C-1 | 2.3 | E-10 | 3.0 | D-1/D-4 | 4,280/1,830 |
| Example 57 | J-57 | A-9 | 100 | B-4 | 14.0 | C-1 | 2.3 | E-12 | 3.0 | D-1/D-4 | 4,280/1,830 |
| Example 58 | J-58 | A-9 | 100 | B-4 | 14.0 | C-1 | 2.3 | E-14 | 3.0 | D-1/D-4 | 4,280/1,830 |
| Example 59 | J-59 | A-9 | 100 | B-4 | 14.0 | C-1 | 2.3 | E-17 | 3.0 | D-1/D-4 | 4,280/1,830 |
| Example 60 | J-60 | A-9 | 100 | B-4 | 14.0 | C-1 | 2.3 | E-18 | 3.0 | D-1/D-4 | 4,280/1,830 |
| Example 61 | J-61 | A-9 | 100 | B-4 | 14.0 | C-1 | 2.3 | E-26 | 3.0 | D-1/D-4 | 4,280/1,830 |
| Example 62 | J-62 | A-10 | 100 | B-4 | 14.0 | C-1 | 2.3 | E-1 | 3.0 | D-1/D-4 | 4,280/1,830 |
| Example 63 | J-63 | A-11 | 100 | B-4 | 14.0 | C-1 | 2.3 | E-1 | 3.0 | D-1/D-4 | 4,280/1,830 |
| Example 64 | J-64 | A-1 | 100 | B-1 | 14.0 | C-1 | 2.3 | E-1 | 3.0 | D-1/D-4 | 4,280/1,830 |
| Example 65 | J-65 | A-1 | 100 | B-3 | 14.0 | C-1 | 2.3 | E-1 | 3.0 | D-1/D-4 | 4,280/1,830 |
| Example 66 | J-66 | A-1 | 100 | B-5 | 14.0 | C-1 | 2.3 | E-1 | 3.0 | D-1/D-4 | 4,280/1,830 |
| Example 67 | J-67 | A-1 | 100 | B-6 | 14.0 | C-1 | 2.3 | E-1 | 3.0 | D-1/D-4 | 4,280/1,830 |
| Example 68 | J-68 | A-1 | 100 | B-4 | 14.0 | C-2 | 2.3 | E-1 | 3.0 | D-1/D-4 | 4,280/1,830 |
| Example 69 | J-69 | A-1 | 100 | B-4 | 14.0 | C-3 | 2.3 | E-1 | 3.0 | D-1/D-4 | 4,280/1,830 |
| Example 70 | J-70 | A-1 | 100 | B-4 | 14.0 | C-4 | 2.3 | E-1 | 3.0 | D-1/D-4 | 4,280/1,830 |
| Example 71 | J-71 | A-1 | 100 | B-4 | 14.0 | C-5 | 2.3 | E-1 | 3.0 | D-1/D-4 | 4,280/1,830 |
| Example 72 | J-72 | A-1 | 100 | B-4 | 14.0 | C-1 | 2.3 | E-1 | 0.3 | D-1/D-4 | 4,280/1,830 |
| Example 73 | J-73 | A-1 | 100 | B-4 | 14.0 | C-1 | 2.3 | E-1 | 1.5 | D-1/D-4 | 4,280/1,830 |
| Example 74 | J-74 | A-1 | 100 | B-4 | 14.0 | C-1 | 2.3 | E-1 | 6.0 | D-1/D-4 | 4,280/1,830 |
| Example 75 | J-75 | A-1 | 100 | B-4 | 14.0 | C-1 | 2.3 | E-1 | 10.0 | D-1/D-4 | 4,280/1,830 |

TABLE 7-continued

| Radiation-sensitive resin composition | | (A) Polymer type | content (parts by mass) | (B) Acid generating agent type | content (parts by mass) | (C) Acid diffusion control agent type | content (parts by mass) | (E) Polymer type | content (parts by mass) | (D) solvent type | content (parts by mass) |
|---|---|---|---|---|---|---|---|---|---|---|---|
| Example 76 | J-76 | A-1 | 100 | B-4 | 14.0 | C-1 | 2.3 | E-1 | 25.0 | D-1/D-4 | 4,280/1,830 |
| Example 77 | J-77 | A-1 | 100 | B-4 | 14.0 | C-1 | 2.3 | E-1/E-27 | 0.01/1.0 | D-1/D-4 | 4,280/1,830 |
| Example 78 | J-78 | A-1 | 100 | B-4 | 14.0 | C-1 | 2.3 | E-1/E-27 | 1.0/1.0 | D-1/D-4 | 4,280/1,830 |
| Example 79 | J-79 | A-1 | 100 | B-4 | 14.0 | C-1 | 2.3 | E-1/E-27 | 10.0/1.0 | D-1/D-4 | 4,280/1,830 |
| Comparative Example 12 | CJ-12 | A-1 | 100 | B-4 | 14.0 | C-1 | 2.3 | E-27 | 3.0 | D-1/D-4 | 4,280/1,830 |
| Comparative Example 13 | CJ-13 | A-1 | 100 | B-4 | 14.0 | C-1 | 2.3 | E-30 | 3.0 | D-1/D-4 | 4,280/1,830 |
| Comparative Example 14 | CJ-14 | A-1 | 100 | B-4 | 14.0 | C-1 | 2.3 | E-31 | 3.0 | D-1/D-4 | 4,280/1,830 |
| Comparative Example 15 | CJ-15 | A-1 | 100 | B-4 | 14.0 | C-1 | 2.3 | E-32 | 3.0 | D-1/D-4 | 4,280/1,830 |
| Comparative Example 16 | CJ-16 | A-1 | 100 | B-4 | 14.0 | C-1 | 2.3 | E-34 | 3.0 | D-1/D-4 | 4,280/1,830 |
| Comparative Example 17 | CJ-17 | A-1 | 100 | B-4 | 14.0 | C-1 | 2.3 | E-36 | 3.0 | D-1/D-4 | 4,280/1,830 |
| Comparative Example 18 | CJ-18 | A-1 | 100 | B-4 | 14.0 | C-1 | 2.3 | E-37 | 3.0 | D-1/D-4 | 4,280/1,830 |

Formation of Resist Pattern Using Positive-Tone Radiation-Sensitive Resin Composition for EUV Exposure An underlayer antireflective film having an average thickness of 105 nm was formed by applying a composition for underlayer antireflective film formation ("ARC66," available from Brewer Science, Inc.) on the surface of a 12-inch silicon wafer using a spin-coater ("CLEAN TRACK ACT 12," available from Tokyo Electron Limited), and thereafter heating the composition at 205° C. for 60 sec. Each radiation-sensitive resin composition for EUV exposure prepared as described above was applied on the underlayer antireflective film using the spin-coater, and subjected to PB at 130° C. for 60 sec. Thereafter, by cooling at 23° C. for 30 sec, a resist film having an average thickness of 55 nm was formed. Next, the resist pattern was exposed using an EUV exposure system ("NXE3300," available from ASML Co.) with NA of 0.33 under an illumination condition of Conventional s=0.89, and with a mask of imecDEFECT32FFR02. After the exposure, the resist film was subjected to PEB at 120° C. for 60 sec. Thereafter, the resist film was subjected to development with an alkali by using a 2.38% by mass aqueous TMAH solution. After the development, washing with water was carried out, followed by drying, to form a positive-tone resist pattern (32 nm line-and-space pattern).

Evaluations

The resist patterns formed using the radiation-sensitive resin compositions for EUV exposure were evaluated on the sensitivity and the number of post-development defects in accordance with the following methods. The results are shown in Table 8 below. It is to be noted that line width measurement of the resist patterns was performed using a scanning electron microscope ("CG-5000," available from Hitachi High-Technologies Corporation).

Sensitivity

An exposure dose at which a 32 nm line-and-space pattern was formed in the aforementioned resist pattern formation using the radiation-sensitive resin composition for EUV exposure was defined as an optimum exposure dose, and this optimum exposure dose was adopted as sensitivity (mJ/$cm^2$). The sensitivity was evaluated to be: "favorable" in a case of being no greater than 22 mJ/$cm^2$; and "unfavorable" in a case of being greater than 22 mJ/$cm^2$.

Number of Development Defects

The resist film was exposed at the optimum radiation dose to form a line and space pattern having a line width of 32 nm, and used as a wafer for defect inspection. The number of defects on the wafer for defect inspection was measured using a defect inspection device ("KLA2810," available from KLA-Tencor). The defects measured as described above were categorized into: defects confirmed to be derived from the resist film; and externally-derived foreign matter, and the number of defects ascertained to be derived from the resist film was calculated. The number of post-exposure defects was evaluated to be: "favorable" in a case of the number of defects judged to be derived from the resist film being no greater than 15; and "unfavorable" in a case of the number of such defects being greater than 15.

TABLE 8

| | Radiation-sensitive resin composition | Sensitivity (mJ/$cm^2$) | Number of development defects |
|---|---|---|---|
| Example 52 | J-52 | 19.1 | 0 |
| Example 53 | J-53 | 18.3 | 2 |
| Example 54 | J-54 | 19.4 | 3 |
| Example 55 | J-55 | 19.2 | 1 |
| Example 56 | J-56 | 19.6 | 0 |
| Example 57 | J-57 | 18.6 | 0 |
| Example 58 | J-58 | 18.9 | 3 |
| Example 59 | J-59 | 19.0 | 8 |
| Example 60 | J-60 | 18.6 | 0 |
| Example 61 | J-61 | 19.1 | 4 |
| Example 62 | J-62 | 19.2 | 3 |
| Example 63 | J-63 | 19.4 | 0 |
| Example 64 | J-64 | 19.6 | 2 |
| Example 65 | J-65 | 18.6 | 1 |
| Example 66 | J-66 | 18.9 | 0 |
| Example 67 | J-67 | 18.5 | 0 |
| Example 68 | J-68 | 18.2 | 1 |
| Example 69 | J-69 | 19.2 | 2 |
| Example 70 | J-70 | 19.7 | 1 |
| Example 71 | J-71 | 19.2 | 9 |
| Example 72 | J-72 | 18.7 | 9 |
| Example 73 | J-73 | 18.9 | 2 |
| Example 74 | J-74 | 19.2 | 0 |

TABLE 8-continued

| | Radiation-sensitive resin composition | Sensitivity (mJ/cm²) | Number of development defects |
|---|---|---|---|
| Example 75 | J-75 | 19.1 | 4 |
| Example 76 | J-76 | 19.4 | 8 |
| Example 77 | J-77 | 19.8 | 10 |
| Example 78 | J-78 | 19.2 | 2 |
| Example 79 | J-79 | 19.1 | 1 |
| Comparative Example 12 | CJ-12 | 24.1 | 151 |
| Comparative Example 13 | CJ-13 | 25.5 | 219 |
| Comparative Example 14 | CJ-14 | 25.1 | 279 |
| Comparative Example 15 | CJ-15 | 24.9 | 180 |
| Comparative Example 16 | CJ-16 | 25.6 | 194 |
| Comparative Example 17 | CJ-17 | 25.2 | 207 |
| Comparative Example 18 | CJ-18 | 24.9 | 167 |

From the results in Table 8, it is revealed that when the radiation-sensitive resin compositions of the Examples were used for EUV exposure, the sensitivity and the post-development defect performance were favorable. In contrast, in the case of the Comparative Examples, each characteristic was inferior compared to the Examples. Thus, in the case of using the radiation-sensitive resin compositions of the Examples for EUV exposure, a resist pattern can be formed with high sensitivity, and having superior water repellency and few defects.

Preparation of Negative-Tone Radiation-Sensitive Resin Composition for ArF Exposure, Formation of Resist Pattern Using this Composition, and Evaluation Thereof

Example 80

A radiation-sensitive resin composition (J-80) was prepared by: mixing 100 parts by mass of (A-1) as the polymer (A), 14.0 parts by mass of (B-5) as the acid generating agent (B), 2.3 parts by mass of (C-3) as the acid diffusion control agent (C), 3.0 parts by mass of (E-18) (solid content) as the polymer (E), and 3,230 parts by mass of a mixed solvent of (D-1)/(D-2)/(D-3) as the solvent (D), and filtering a resulting mixture through a membrane filter having a pore size of 0.2 μm.

In the resist pattern formation using the negative-tone radiation-sensitive resin composition for ArF exposure, a resist film was formed, ArF exposure was carried out, and PEB was conducted by a similar operation except that the negative-tone radiation-sensitive resin composition for ArF exposure (J-80) prepared as described above was used as the radiation-sensitive resist composition. Thereafter, a negative-tone resist pattern (40 nm line-and-space pattern) was formed by: subjecting the resist film to development with an organic solvent using n-butyl acetate as an organic solvent developer solution, and drying.

The resist pattern formed by using the negative-tone radiation-sensitive resin composition for ArF exposure and the resist film before ArF exposure were evaluated similarly to the evaluations of the resist patterns formed by using the positive-tone radiation-sensitive resin compositions for ArF exposure. As a result, the radiation-sensitive resin composition of Example 80 was favorable in terms of the sensitivity, the post-PB receding contact angle performance, and the post-development defect performance, even in the case of forming the negative-tone resist pattern by ArF exposure.

According to the radiation-sensitive resin composition and the method of forming a resist pattern of the embodiments of the present invention, a resist pattern can be formed with favorable sensitivity to exposure light, and having superior water repellency and few defects. The polymer of the still another embodiment of the present invention can be suitably used as a polymer component of the radiation-sensitive resin composition of the one embodiment of the present invention. The compound of the yet another embodiment of the present invention can be suitably used as a monomer of the polymer of the still another embodiment of the present invention. Thus, these can be suitably used in manufacturing of a semiconductor device and the like, in which further progress of miniaturization is expected in the future.

Obviously, numerous modifications and variations of the present invention are possible in light of the above teachings. It is therefore to be understood that within the scope of the appended claims, the invention may be practiced otherwise than as specifically described herein.

What is claimed is:

1. A radiation-sensitive resin composition comprising:

a first polymer comprising a structural unit comprising an acid-labile group;

a second polymer comprising a structural unit represented by formula (1); and a radiation-sensitive acid generator, (1)

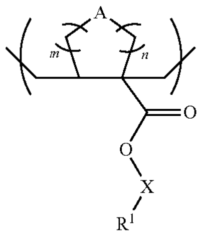

wherein, in the formula (1), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group comprising a fluorine atom.

2. The radiation-sensitive resin composition according to claim 1, wherein $R^1$ in the formula (1) represents a group defined as (1-1) or (1-2):

(1-1): a group represented by *—COO—$R^{1a}$, wherein $R^{1a}$ represents a substituted or unsubstituted monovalent fluorinated hydrocarbon group having 1 to 20 carbon atoms, or a monovalent organic group comprising —O—, —CO—, or —COO— between two carbon atoms in a C—C bond constituting a substituted or unsubstituted monovalent fluorinated hydrocarbon group having 2 to 20 carbon atoms; and * denotes a site of bonding to X in the formula (1); and (1-2): a substituted or unsubstituted monovalent fluorinated hydrocarbon group having 1 to 20 carbon atoms, or a group comprising —O—, —CO—, or —COO— between two carbon atoms in a C—C bond constituting a substituted or unsubstituted monovalent fluorinated hydrocarbon group having 2 to 20 carbon atoms, wherein the group defined as (1-2) does not fall under the group defined as (1-1).

3. The radiation-sensitive resin composition according to claim 2, wherein $R^{1a}$ in the group defined as (1-1) represents a substituted or unsubstituted monovalent fluorinated hydrocarbon group having 1 to 20 carbon atoms, —$R^{1b}$—COO—$R^{1c}$, or —$R^{1d}$—O—$R^{1e}$, wherein $R^{1b}$ represents a substituted or unsubstituted divalent hydrocarbon group having 1 to 20 carbon atoms, a substituted or unsubstituted divalent fluorinated hydrocarbon group having 1 to 20 carbon atoms, or a divalent organic group comprising a lactone structure and having 4 to 20 carbon atoms, $R^{1c}$ represents a substituted or unsubstituted monovalent hydrocarbon group having 1 to 20 carbon atoms or a substituted or unsubstituted monovalent fluorinated hydrocarbon group having 1 to 20 carbon atoms, wherein at least one of $R^{1b}$ and $R^{1c}$ comprises a fluorine atom, $R^{1d}$ represents a substituted or unsubstituted divalent hydrocarbon group having 1 to 20 carbon atoms, a substituted or unsubstituted divalent fluorinated hydrocarbon group having 1 to 20 carbon atoms, or a divalent organic group comprising a lactone structure and having 4 to 20 carbon atoms, and $R^{1e}$ represents a substituted or unsubstituted monovalent hydrocarbon group having 1 to 20 carbon atoms, a substituted or unsubstituted monovalent fluorinated hydrocarbon group having 1 to 20 carbon atoms, or —$R^{1f}$—O—$R^{1g}$, wherein $R^{1f}$ represents a substituted or unsubstituted divalent hydrocarbon group having 1 to 20 carbon atoms or a substituted or unsubstituted divalent fluorinated hydrocarbon group having 1 to 20 carbon atoms, and $R^{1g}$ represents a substituted or unsubstituted monovalent hydrocarbon group having 1 to 20 carbon atoms or a substituted or unsubstituted monovalent fluorinated hydrocarbon group having 1 to 20 carbon atoms, wherein at least one of $R^{1d}$ and $R^{1e}$ comprises a fluorine atom.

4. The radiation-sensitive resin composition according to claim 2, wherein the group defined as (1-2) represents a substituted or unsubstituted monovalent fluorinated hydrocarbon group having 1 to 20 carbon atoms,*—CO—$R^{2a}$, *—$R^{2b}$—COO—$R^{2c}$, or *—$R^{2d}$—O—$R^{2e}$, wherein $R^{2a}$ represents a substituted or unsubstituted monovalent fluorinated hydrocarbon group having 10 to 20 carbon atoms, $R^{2b}$ represents a substituted or unsubstituted divalent hydrocarbon group having 1 to 20 carbon atoms, a substituted or unsubstituted divalent fluorinated hydrocarbon group having 1 to 20 carbon atoms, or a divalent organic group comprising a lactone structure and having 4 to 20 carbon atoms, $R^{2c}$ represents a substituted or unsubstituted monovalent hydrocarbon group having 1 to 20 carbon atoms or a substituted or unsubstituted monovalent fluorinated hydrocarbon group having 1 to 20 carbon atoms, wherein at least one of $R^{2b}$ and $R^{2c}$ comprises a fluorine atom, $R^{2d}$ represents a substituted or unsubstituted divalent hydrocarbon group having 1 to 20 carbon atoms, a substituted or unsubstituted divalent fluorinated hydrocarbon group having 1 to 20 carbon atoms, or a divalent organic group comprising a lactone structure and having 4 to 20 carbon atoms, and $R^{2e}$ represents a substituted or unsubstituted monovalent hydrocarbon group having 1 to 20 carbon atoms, a substituted or unsubstituted monovalent fluorinated hydrocarbon group having 1 to 20 carbon atoms, or —$R^{2f}$—O—$R^{2g}$, wherein $R^{2f}$ represents a substituted or unsubstituted divalent hydrocarbon group having 1 to 20 carbon atoms or a substituted or unsubstituted divalent fluorinated hydrocarbon group having 1 to 20 carbon atoms, and $R^{2g}$ represents a substituted or unsubstituted monovalent hydrocarbon group having 1 to 20 carbon atoms or a substituted or unsubstituted monovalent fluorinated hydrocarbon group having 1 to 20 carbon atoms, wherein at least one of $R^{2d}$ and $R^{2e}$ comprises a fluorine atom.

5. The radiation-sensitive resin composition according to claim 1, wherein X in the formula (1) represents a single bond, a substituted or unsubstituted divalent hydrocarbon group having 1 to 20 carbon atoms, a divalent organic group comprising a lactone structure and having 4 to 20 carbon atoms, —$X^1$—O—, or —$X^2$—NH—, wherein $X^1$ and $X^2$ each independently represent a divalent hydrocarbon group having 1 to 20 carbon atoms.

6. The radiation-sensitive resin composition according to claim 5, wherein each divalent hydrocarbon group having 1 to 20 carbon atoms which may be represented by each of X in the formula (1), $X^1$, and $X^2$ independently represents a divalent chain hydrocarbon group having 1 to 4 carbon atoms, a divalent alicyclic hydrocarbon group having 6 to 10 carbon atoms, or a divalent aromatic hydrocarbon group having 6 to 10 carbon atoms.

7. A method of forming a resist pattern, the method comprising:

applying the radiation-sensitive resin composition according to claim 1 directly or indirectly on a substrate to form a resist film;

exposing the resist film; and developing the resist film exposed.

8. The method according to claim 7, wherein $R^1$ in the formula (1) is a group defined as (1-1) or (1-2):

(1-1): a group represented by *—COO—$R^{1a}$, wherein $R^{1a}$ represents a substituted or unsubstituted monovalent fluorinated hydrocarbon group having 1 to 20 carbon atoms, or a monovalent organic group comprising —O—, —CO—, or —COO— between two carbon atoms in a C—C bond constituting a substituted or unsubstituted monovalent fluorinated hydrocarbon group having 2 to 20 carbon atoms; and * denotes a site of bonding to X in the formula (1); and (1-2): a substituted or unsubstituted monovalent fluorinated hydrocarbon group having 1 to 20 carbon atoms, or a group comprising —O—, —CO—, or —COO— between two carbon atoms in a C—C bond constituting a substituted or unsubstituted monovalent fluorinated hydrocarbon group having 2 to 20 carbon atoms, wherein the group defined as (1-2) does not fall under the group defined as (1-1).

9. The method according to claim 7, wherein X in the formula (1) represents a single bond, a substituted or unsubstituted divalent hydrocarbon group having 1 to 20 carbon atoms, a divalent organic group comprising a lactone structure and having 4 to 20 carbon atoms, —$X^1$—O—, or —$X^2$—NH—, wherein $X^1$ and $X^2$ each independently represent a divalent hydrocarbon group having 1 to 20 carbon atoms.

10. The method according to claim 9, wherein each divalent hydrocarbon group having 1 to 20 carbon atoms which may be represented by each of X in the formula (1), $X^1$, and $X^2$ independently represents a divalent chain hydrocarbon group having 1 to 4 carbon atoms, a divalent alicyclic hydrocarbon group having 6 to 10 carbon atoms, or a divalent aromatic hydrocarbon group having 6 to 10 carbon atoms.

11. A polymer comprising a structural unit represented by formula (1):

(1)

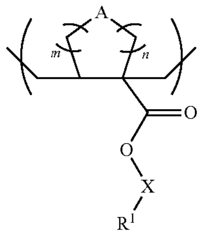

wherein, in the formula (1), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group comprising a fluorine atom.

12. The polymer according to claim 11, wherein $R^1$ in the formula (1) is a group defined as (1-1) or (1-2):

(1-1): a group represented by *—COO—$R^{1a}$, wherein $R^{1a}$ represents a substituted or unsubstituted monovalent fluorinated hydrocarbon group having 1 to 20 carbon atoms, or a monovalent organic group comprising —O—, —CO—, or —COO— between two carbon atoms in a C—C bond constituting a substituted or unsubstituted monovalent fluorinated hydrocarbon group having 2 to 20 carbon atoms; and * denotes a site of bonding to X in the formula (1); and (1-2): a substituted or unsubstituted monovalent fluorinated hydrocarbon group having 1 to 20 carbon atoms, or a group comprising —O—, —CO—, or —COO— between two carbon atoms in a C—C bond constituting a substituted or unsubstituted monovalent fluorinated hydrocarbon group having 2 to 20 carbon atoms, wherein the group defined as (1-2) does not fall under the group defined as (1-1).

13. The polymer according to claim 11, wherein X in the formula (1) represents a single bond, a substituted or unsubstituted divalent hydrocarbon group having 1 to 20 carbon atoms, a divalent organic group comprising a lactone structure and having 4 to 20 carbon atoms, —$X^1$—O—, or —$X^2$—NH—, wherein $X^1$ and $X^2$ each independently represent a divalent hydrocarbon group having 1 to 20 carbon atoms.

14. The polymer according to claim 13, wherein each divalent hydrocarbon group having 1 to 20 carbon atoms which may be represented by each of X in the formula (1), $X^1$, and $X^2$ independently represents a divalent chain hydrocarbon group having 1 to 4 carbon atoms, a divalent alicyclic hydrocarbon group having 6 to 10 carbon atoms, or a divalent aromatic hydrocarbon group having 6 to 10 carbon atoms.

15. A compound represented by formula (i):

(i)

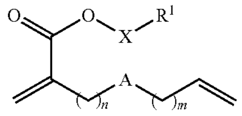

wherein, in the formula (i), A represents an oxygen atom or a sulfur atom; a sum of m and n is 2 or 3, wherein m is 1 or 2, and n is 1 or 2; X represents a single bond or a divalent organic group having 1 to 20 carbon atoms; and $R^1$ represents a monovalent organic group comprising a fluorine atom.

16. The compound according to claim 15, wherein $R^1$ in the formula (i) is a group defined as (1-1) or (1-2):

(1-1): a group represented by *—COO—$R^{1a}$, wherein $R^{1a}$ represents a substituted or unsubstituted monovalent fluorinated hydrocarbon group having 1 to 20 carbon atoms, or a monovalent organic group comprising —O—, —CO—, or —COO— between two carbon atoms in a C—C bond constituting a substituted or unsubstituted monovalent fluorinated hydrocarbon group having 2 to 20 carbon atoms; and * denotes a site of bonding to X in the formula (i); and (1-2): a substituted or unsubstituted monovalent fluorinated hydrocarbon group having 1 to 20 carbon atoms, or a group comprising —O—, —CO—, or —COO— between two carbon atoms in a C—C bond constituting a substituted or unsubstituted monovalent fluorinated hydrocarbon group having 2 to 20 carbon atoms, wherein the group defined as (1-2) does not fall under the group defined as (1-1).

17. The compound according to claim 15, wherein X in the formula (i) represents a single bond, a substituted or unsubstituted divalent hydrocarbon group having 1 to 20 carbon atoms, a divalent organic group comprising a lactone structure and having 4 to 20 carbon atoms, —$X^1$—O—, or —$X^2$—NH—, wherein $X^1$ and $X^2$ each independently represent a divalent hydrocarbon group having 1 to 20 carbon atoms.

18. The compound according to claim 17, wherein each divalent hydrocarbon group having 1 to 20 carbon atoms which may be represented by each of X in the formula (i), $X^1$, and $X^2$ independently represents a divalent chain hydrocarbon group having 1 to 4 carbon atoms, a divalent alicyclic hydrocarbon group having 6 to 10 carbon atoms, or a divalent aromatic hydrocarbon group having 6 to 10 carbon atoms.

* * * * *